(12) United States Patent
Webb et al.

(10) Patent No.: US 8,551,150 B1
(45) Date of Patent: *Oct. 8, 2013

(54) METHOD AND SYSTEM FOR OPTICAL STIMULATION OF NERVES

(71) Applicant: Lockheed Martin Corporation, Bethesda, MD (US)

(72) Inventors: James S. Webb, Seattle, WA (US); Mark P. Bendett, Cherry Hill, NJ (US); Heather A. Ralph, Seattle, WA (US); Jonathon D. Wells, Seattle, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,379

(22) Filed: Nov. 7, 2012

Related U.S. Application Data

(62) Division of application No. 13/225,408, filed on Sep. 3, 2011, now Pat. No. 8,317,848, which is a division of application No. 11/971,874, filed on Jan. 9, 2008, now Pat. No. 8,012,189.

(60) Provisional application No. 60/884,619, filed on Jan. 11, 2007, provisional application No. 60/885,879, filed on Jan. 19, 2007, provisional application No. 60/964,634, filed on Aug. 13, 2007.

(51) Int. Cl.
*A61N 5/06* (2006.01)

(52) U.S. Cl.
USPC .............................................. 607/89; 607/88

(58) Field of Classification Search
USPC .......................................... 607/2, 42, 88, 89
See application file for complete search history.

(56) References Cited

U.S. PATENT DOCUMENTS

| 4,064,872 | A | 12/1977 | Caplan |
| 4,215,694 | A | 8/1980 | Isakov et al. |
| 4,296,995 | A | 10/1981 | Bickel |
| 4,558,703 | A | 12/1985 | Mark |
| 4,566,935 | A | 1/1986 | Hornbeck |
| 4,596,992 | A | 6/1986 | Hornbeck |
| 4,671,285 | A | 6/1987 | Walker |
| 4,681,791 | A | 7/1987 | Shibahashi et al. |
| 4,724,835 | A | 2/1988 | Liss et al. |

(Continued)

FOREIGN PATENT DOCUMENTS

WO     WO 0025112     5/2000

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Bill Thomson
*Assistant Examiner* — Jeffrey Lipitz
(74) *Attorney, Agent, or Firm* — Charles A. Lemaire; Jonathan M. Rixen; Lemaire Patent Law Firm, P.L.L.C.

(57) ABSTRACT

An optical-signal vestibular-nerve stimulation device and method that provides different nerve stimulation signals to a plurality of different vestibular nerves, including at least some of the three semicircular canal nerves and the two otolith organ nerves. In some embodiments, balance conditions of the person are sensed by the implanted device or external device, and based on the sensed balance conditions, varying laser nerve-stimulation signals are sent to a plurality of the different vestibular nerves.

23 Claims, 12 Drawing Sheets

(56) References Cited

U.S. PATENT DOCUMENTS

| | | |
|---|---|---|
| 4,757,515 A | 7/1988 | Hughes |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,791,231 A | 8/1998 | Cohn et al. |
| 5,792,051 A | 8/1998 | Chance |
| 5,796,889 A | 8/1998 | Xu et al. |
| 5,799,030 A | 8/1998 | Brenner |
| 5,827,265 A | 10/1998 | Glinsky et al. |
| 5,851,223 A | 12/1998 | Liss et al. |
| 5,899,865 A | 5/1999 | Chance |
| 5,913,884 A | 6/1999 | Trauner et al. |
| 5,957,960 A | 9/1999 | Chen et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,240,308 B1 | 5/2001 | Hardy et al. |
| 6,246,892 B1 | 6/2001 | Chance |
| 6,254,637 B1 | 7/2001 | Lee et al. |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,722 B1 | 7/2003 | Abe |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,131,968 B2 | 11/2006 | Bendett et al. |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,351,241 B2 | 4/2008 | Bendett et al. |
| 7,391,561 B2 | 6/2008 | Di Teodoro et al. |
| 7,402,167 B2 | 7/2008 | Nemenov |
| 7,488,341 B2 | 2/2009 | Merfeld |
| 7,598,088 B2 | 10/2009 | Balas |
| 7,647,112 B2 | 1/2010 | Tracey et al. |
| 7,654,750 B2 | 2/2010 | Brenner et al. |
| 7,736,382 B2 | 6/2010 | Webb et al. |
| 7,747,318 B2 | 6/2010 | John et al. |

| | | |
|---|---|---|
| 7,756,588 B2 | 7/2010 | Jog et al. |
| 7,771,374 B2 | 8/2010 | Slatkine |
| 7,776,631 B2 | 8/2010 | Miles |
| 7,787,170 B2 | 8/2010 | Patel et al. |
| 7,797,029 B2 | 9/2010 | Gibson et al. |
| 7,801,601 B2 | 9/2010 | Maschino et al. |
| 7,803,454 B2 | 9/2010 | Toepel |
| 7,833,257 B2 | 11/2010 | Walsh, Jr. et al. |
| 7,865,236 B2 | 1/2011 | Cory et al. |
| 7,883,535 B2 | 2/2011 | Cantin et al. |
| 7,899,512 B2 | 3/2011 | Labadie et al. |
| 7,904,139 B2 | 3/2011 | Chance |
| 7,914,842 B1 | 3/2011 | Greenberg et al. |
| 7,951,181 B2 | 5/2011 | Mahadevan-Jansen et al. |
| 7,962,192 B2 | 6/2011 | Bodduluri |
| 7,988,688 B2 | 8/2011 | Webb et al. |
| 8,078,263 B2 | 12/2011 | Zeman et al. |
| 8,136,531 B2 | 3/2012 | Chariff |
| 8,197,539 B2 | 6/2012 | Nasiatka et al. |
| 8,207,211 B2 | 6/2012 | Wharton et al. |
| 2002/0002391 A1 | 1/2002 | Gerdes |
| 2003/0236458 A1 | 12/2003 | Hochman |
| 2004/0143190 A1 | 7/2004 | Schnitzer |
| 2004/0225339 A1 | 11/2004 | Yaroslavsky et al. |
| 2005/0099824 A1 | 5/2005 | Dowling et al. |
| 2005/0143789 A1 | 6/2005 | Whitehurst et al. |
| 2006/0149337 A1 | 7/2006 | John |
| 2006/0161218 A1 | 7/2006 | Danilov |
| 2006/0167564 A1 | 7/2006 | Flaherty et al. |
| 2006/0276861 A1 | 12/2006 | Lin |
| 2007/0053996 A1 | 3/2007 | Boyden et al. |
| 2007/0054319 A1 | 3/2007 | Boyden et al. |
| 2007/0142874 A1 | 6/2007 | John |
| 2007/0191906 A1 | 8/2007 | Iyer et al. |
| 2007/0261127 A1 | 11/2007 | Boyden et al. |
| 2008/0009748 A1 | 1/2008 | Gratton et al. |
| 2008/0077200 A1 | 3/2008 | Bendett et al. |
| 2008/0161697 A1 | 7/2008 | Chance |
| 2008/0221640 A1 | 9/2008 | Overstreet et al. |
| 2009/0030327 A1 | 1/2009 | Chance |
| 2009/0062685 A1 | 3/2009 | Bergethon et al. |
| 2009/0163982 A1 | 6/2009 | deCharms |
| 2009/0177247 A1 | 7/2009 | Neal et al. |
| 2009/0177255 A1 | 7/2009 | Merfeld |

OTHER PUBLICATIONS

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Boyden, Edward S., et al., "Millisecond-timescale, genetically targeted optical control of neural activity", "Nature Neuroscience", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregularion of Biol. Activity by Photochromic Reagents, 3. Photoreg. of Bioelectricity by Acetylcholine Receptor Inh", "Proc. Natl. Acad. Sci.", 1969, pp. 1230-1234, vol. 64, No. 4.

Dodt, H.-U., et al., "Precisely Localized LTD in the Neocortex Revealed by Infrared-Guided Laser Stimulation.", "Science", Oct. 1, 1999, pp. 110-113, vol. 286.

Dodt, H.-U., et al., "Circuitry of rat barrel cortex investigated by infrared-guided laser stimulation", "NeuroReport", Mar. 24, 2003, pp. 623-627, vol. 14, No. 4.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Izzo, et al., "Laser Stimulation of the Auditory Nerve", "Lasers in Surgery and Medicine", 2006, Publisher: Wiley-Liss, Inc.

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , pp. 064036, vol. 10, No. 6.

Princeton Lightwave (Company), "High Power Multimode Laser Arrays", "www.princetonlightwave.com/content/pli_high_power_multimode_laser_arrays.pdf", Dec. 24, 2005 downloaded.

Princeton Lightwave (Company), "High Power Water Cooled Laser Stack", "http://www.princetonlightwave.com/content/pli_high_power_multimode_laser_stacks.pdf", Oct. 24, 2005 downloaded.

Princeton Lightwave (Company), "Duplicate Do Not Use High Power Water Cooled Laser Stack", "www.princetonlightwave.com", Oct. 24, 2005 downloaded.

Princeton Lightwave (Company), "High Power Single Element Laser", "www.princetonlightwave.com/content/HP%20Single%20Element%20Laser%20version%202.pdf", 2005 (downloaded).

Rolfe, "In Vivo Near-Infrared Spectroscopy", "Annu. Rev. Biomed. Eng.", 2000, pp. 715-754 , vol. 2.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics", Nov. 2005, pp. 064003-1-064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al. , "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al. , "Channelrhodopsin-2 and optical control of excitable cells", "Nature Methods", Sep. 21, 2006, pp. 785-792, vol. 3, No. 10.

Matthies, et al., "Direct Brainstem Recording of Auditory Evoked Potentials During Vestibular Schwannoma Resection: Nuclear BAEP Recording", "J. Neurosurg.", Jun. 1997, pp. 1057-1062, vol. 86.

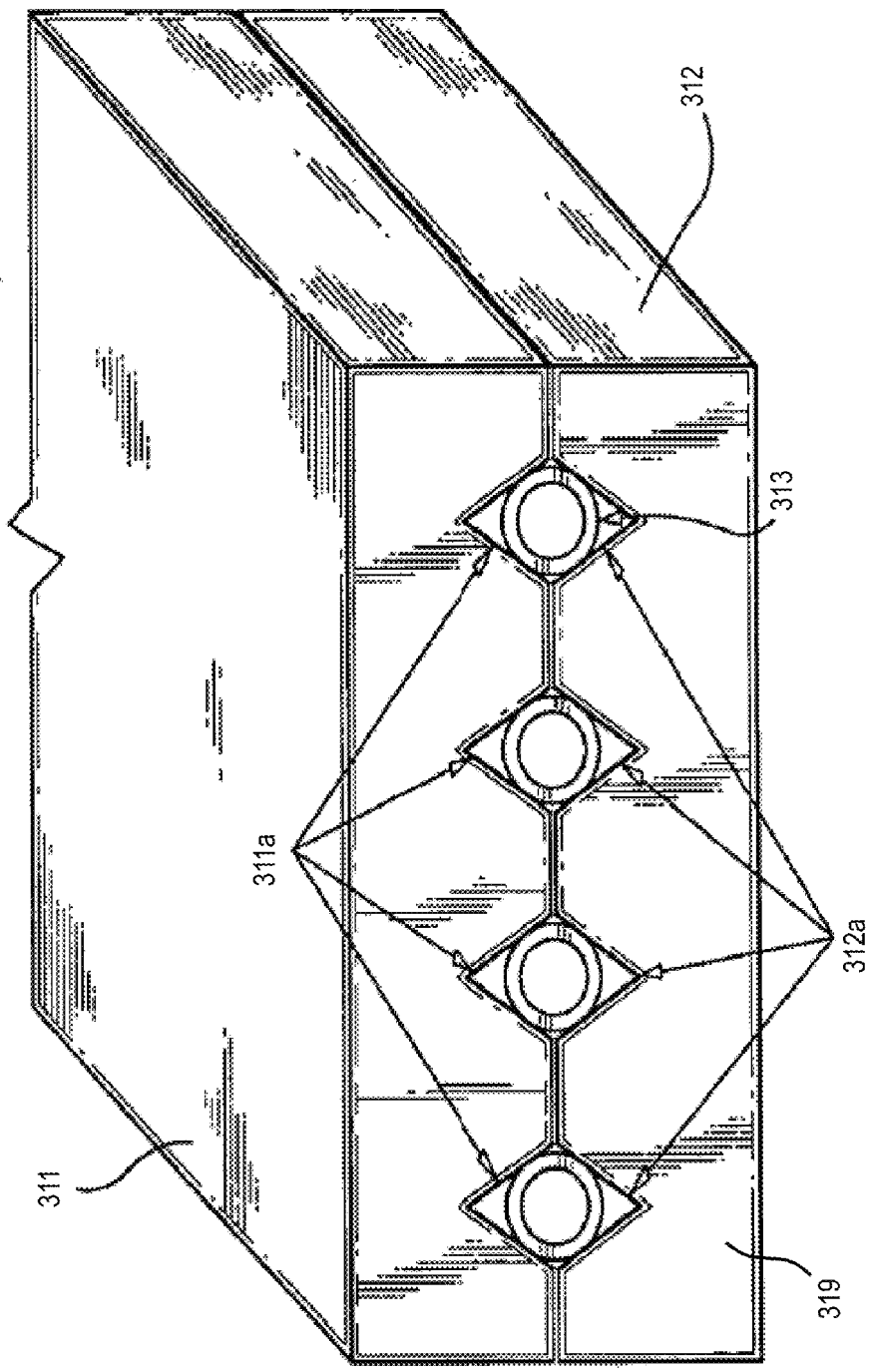
FIG. 3.1

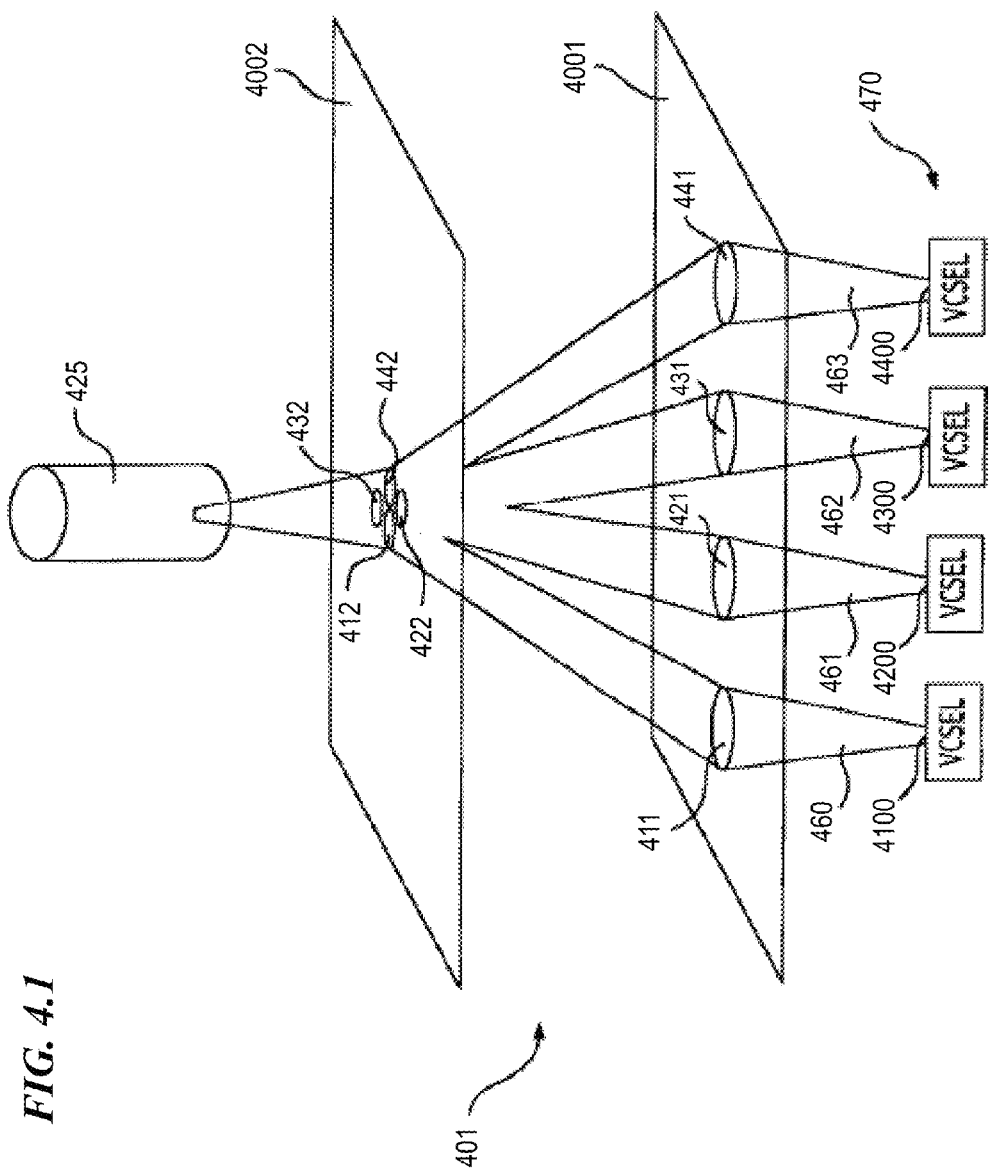
FIG. 4.1

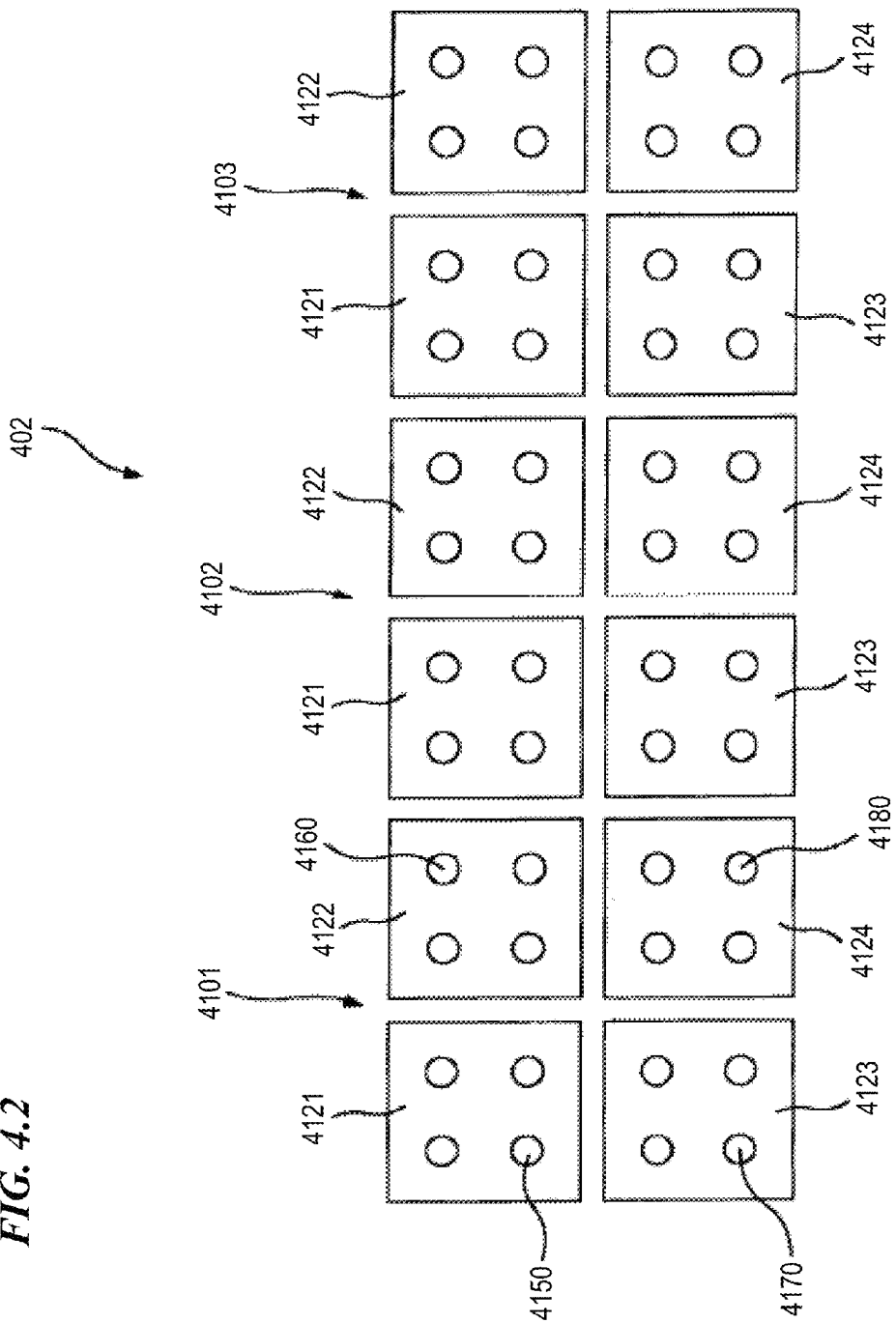
FIG. 4.2

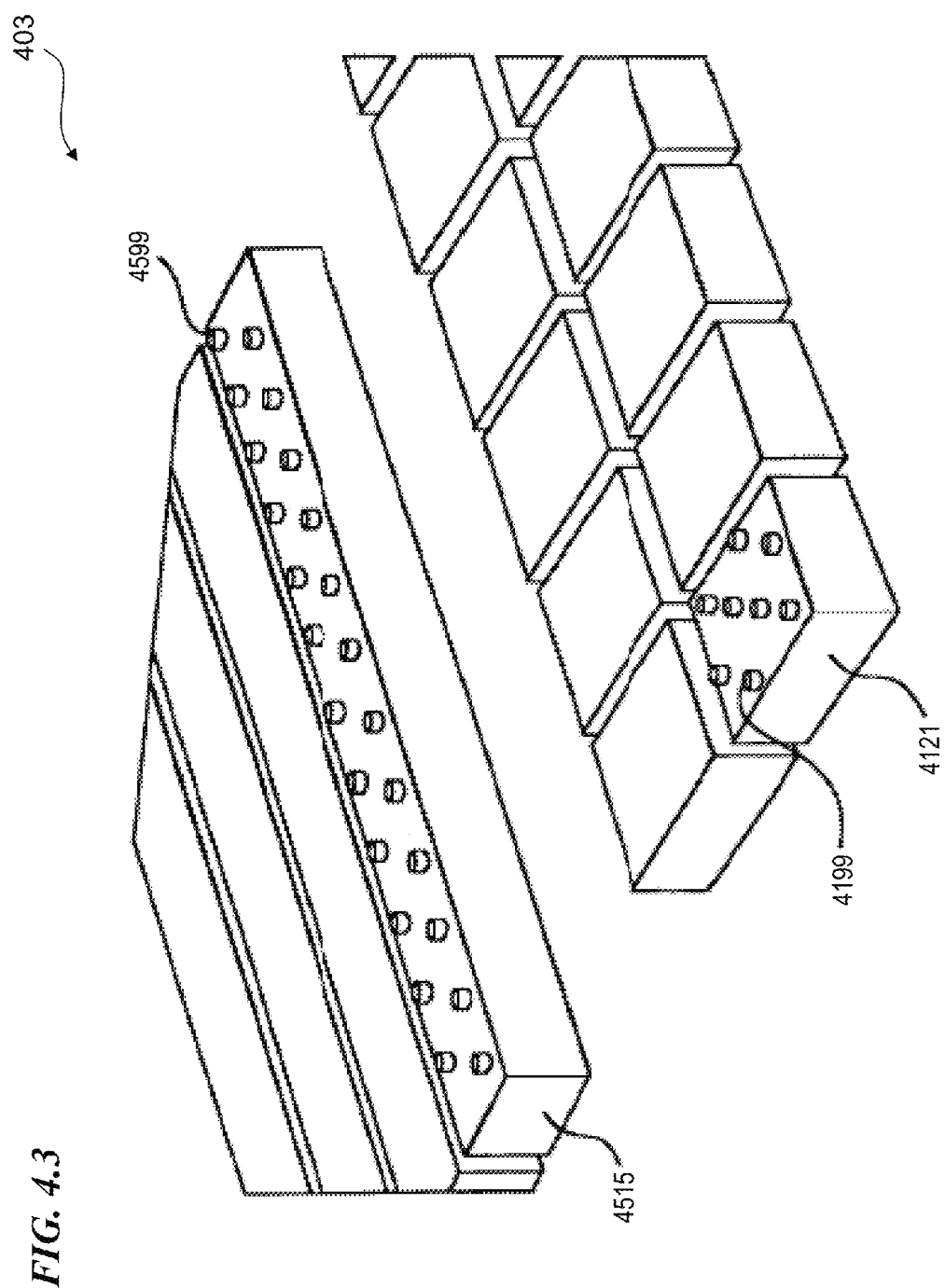

METHOD AND SYSTEM FOR OPTICAL STIMULATION OF NERVES

CROSS-REFERENCE TO RELATED APPLICATIONS

This is a divisional of and claims benefit of
U.S. patent application Ser. No. 13/225,408 filed Sep. 3, 2011, titled "VESTIBULAR IMPLANT AND METHOD FOR OPTICAL STIMULATION OF NERVES", (issued as U.S. Pat. No. 8,317,848 on Nov. 27, 2012), which is a divisional of U.S. patent application Ser. No. 11/971,874 filed Jan. 9, 2008, titled "METHOD AND VESTIBULAR IMPLANT USING OPTICAL STIMULATION OF NERVES" (issued as U.S. Pat. No. 8,012,189 on Sep. 6, 2011), which claims benefit of
U.S. Provisional Patent Application No. 60/884,619 filed Jan. 11, 2007, titled "Vestibular Implant Using Infrared Nerve Stimulation"; of
U.S. Provisional Patent Application No. 60/885,879 filed Jan. 19, 2007, titled "Hybrid Optical-Electrical Probes"; and of
U.S. Provisional Patent Application No. 60/964,634 filed Aug. 13, 2007, titled "VCSEL Array Stimulator Apparatus and Method for Light Stimulation of Bodily Tissues";
each of which is incorporated herein by reference in its entirety.

This invention is also related to prior
U.S. patent application Ser. No. 11/257,793 filed Oct. 24, 2005, titled "Apparatus and Method for Optical Stimulation of Nerves and Other Animal Tissue" (which issued as U.S. Pat. No. 7,736,382 on Jun. 15, 2010);
U.S. patent application Ser. No. 11/536,639 filed Sep. 28, 2006, titled "Miniature Apparatus and Method for Optical Stimulation of Nerves and Other Animal Tissue" (which issued as U.S. Pat. No. 7,988,688 on Aug. 2, 2011);
U.S. patent application Ser. No. 11/536,642 filed Sep. 28, 2006, titled "Apparatus and Method for Stimulation of Nerves and Automated Control of Surgical Instruments";
U.S. Provisional Patent Application Ser. No. 60/872,930 filed Dec. 4, 2006, titled "Apparatus and Method for Characterizing Optical Sources Used with Human and Animal Tissues"; and
U.S. patent application Ser. No. 11/948,912 filed Nov. 30, 2007, titled "Apparatus and Method for Characterizing Optical Sources Used with Human and Animal Tissues";
each of which is incorporated herein by reference in its entirety.

FIELD OF THE INVENTION

The invention relates generally to tissue optics (interactions of light with human or animal tissue), and more particularly to methods and implantable apparatus for stimulating nerves of the auditory system in animals, for example, using an implantable device in medical treatments for auditory, balance, and dizziness conditions of the vestibular system using laser light, such as infrared (IR) wavelengths, for optical stimulation of nerves of the inner ear and related bodily systems.

BACKGROUND OF THE INVENTION

A person's inner ear includes the labyrinth, a delicate memberous system of fluid passages that includes both the cochlea (which is part of the auditory system), and the vestibular system (which provides part of the sense of balance). The eyes also provide signals used for balance, as do joint and muscle receptors and the cerebellum. The brain, specifically the vestibular nuclear complex, receives and analyzes the information from these systems, and generates signals that control a person's balance.

Each inner-ear includes three semicircular canals and a vestibule, the region where the semicircular canals converge, and which is close to the cochlea (the hearing organ). The vestibular system also works with the visual system to keep objects in focus when the head is moving.

Interference with, or infection, of the labyrinth can result in a syndrome of ailments called labyrinthitis. The symptoms of labrynthitis include temporary nausea, disorientation, vertigo, and dizziness. Labyrinthitis can be caused by viral infections, bacterial infections, physical blockage of the inner ear, or due to decompression sickness.

Some people lose vestibular hair cells or suffer from balance and dizziness problems that are not readily treatable through therapy and/or drugs. These conditions can be very debilitating, since the affected person must remain still to minimize unpleasant dizziness or feeling continuously "seasick." The condition can also affect their ability to walk or keep their balance in general.

The semicircular canals in the inner ear form three loops that are fluid filled and sense rotation of a person.

Otoliths (earstones) are small particles composed of calcium carbonate supported in a gelatinous matrix in the viscous fluid of the saccule and utricle (the utricle is located in the vestibule, between the semicircular canals and the cochlea within a swelling adjacent to the semicircular canals, and the saccule is closer to the cochlea). The inertia of these small particles (sometimes referred to as stones or crystals) causes them to stimulate hair cells differently when the head moves. The hair cells send signals down sensory nerve fibers via the vestibulocochlear cranial nerve (CN VIII), which are interpreted by the brain as motion. The vestibular nucleus coordinates inputs from the muscles responsible for posture via the spinal cord, information on control, balance, and movements via the cerebellum, and head and neck movements via cranial nerves III, IV, and VI.

The saccule and utricle together make the otolith organs. They are sensitive to gravity and linear acceleration. Because of their orientation in the head, the utricle is sensitive to a change in horizontal movement, and the saccule gives information about vertical acceleration (such as when in an elevator). The otolith organs also provide information to the brain orientation of the head, such as being in a vertical position or prone position, or being face-up or face-down.

When the head is in a normal upright position, the otolith presses on the sensory hair cell receptors. This pushes the hair cell processes down and prevents them from moving side to side. However, when the head is tilted, the pull of gravity on statoconia shift the hair cell processes to the side, distorting them and sending a message to the central nervous system that the head is no longer level but now tilted. The motion sensation from the otoliths is involved in a large number of reflexes. Damage to the otoliths or their central connections can impair ocular and body stabilization.

U.S. Pat. No. 7,225,028 issued to Della Santina et al. on May 29, 2007, and titled "Dual Cochlear/Vestibular Stimulator with Control Signals Derived from Motion and Speech Signals", is incorporated herein by reference. Della Santina et al. describe a system for treating patients affected both by hearing loss and by balance disorders related to vestibular hypofunction and/or malfunction, which includes sensors of sound and head movement, processing circuitry, a power source, and an implantable electrical stimulator capable of stimulating areas of the cochlea and areas of the vestibular system.

U.S. Patent Application Publication No. US 2007/0261127 A1 filed Jul. 24, 2006 by Edward S. Boyden and Karl Deisseroth, titled "LIGHT-ACTIVATED CATION CHANNEL AND USES THEREOF"; U.S. Patent Application Publication No. US 2007/0054319 A1 filed Jul. 24, 2006 by Edward S. Boyden and Karl Deisseroth, titled "LIGHT-ACTIVATED CATION CHANNEL AND USES THEREOF" filed Jul. 24, 2006; and U.S. Patent Application Publication No. US 2007/0053996 A1 filed Jul. 24, 2006 by Edward S. Boyden and Karl Deisseroth, titled "LIGHT-ACTIVATED CATION CHANNEL AND USES THEREOF" are all incorporated herein by reference. These describe compositions and methods for light-activated cation channel proteins and their uses within cell membranes and subcellular regions. They describe proteins, nucleic acids, vectors and methods for genetically targeted expression of light-activated cation channels to specific cells or defined cell populations. In particular the description provides millisecond-timescale temporal control of cation channels using moderate light intensities in cells, cell lines, transgenic animals, and humans. The descriptions provide for optically generating electrical spikes in nerve cells and other excitable cells useful for driving neuronal networks, drug screening, and therapy.

U.S. Pat. No. 6,748,275 issued to Lattner et al. on Jun. 8, 2004, and titled "Vestibular Stimulation System and Method" (herein "Lattner et al. '275 patent"), is incorporated herein by reference. Lattner et al. '275 patent describes an apparatus and method in which the portions of the labyrinth associated with the labyrinthine sense and/or the nerves associated therewith are stimulated to perform at least one of the following functions: augment or control a patient's respiratory function, open the patient's airway, induce sleep, and/or counteract vertigo. Solely as background, FIG. 1A and FIG. 1B are provided to show an environment for the present invention.

FIG. 1A is a perspective view of the labyrinth and associated nerves of prior art embodiment for vestibular stimulation as described in the Lattner et al. '275 patent. (See Lattner et al. '275 patent FIG. 7 and associated written description). The Lattner et al. '275 patent (see column 16, lines 13-45) describes augmenting the respiratory function by inducing stimulation of the vestibular nerve so that the polysynaptic interaction of the vestibular nerve with the nerves associated with respiration can augment the patient's respiratory function. Stimulation of the vestibular nerve is accomplished by stimulating vestibular nerve 42 directly and/or by stimulating one or more of nerve branches 44*a* and 44*b*. In one example, an electrode 82 in direct contact with vestibular nerve provides the stimulation to this nerve. A lead 84 couples the electrode to the source of stimulation energy. Alternatively, or in addition to electrode 82, Lattner et al. '275 contemplates providing electrodes 86*b* in contact with nerve branches 44*a* and 44*b*, respectively, to stimulate the nerve branches, which, in turn, induce stimulation in the vestibular nerve. Leads 54*b* couple electrodes 86*b* to the source of stimulation energy.

Lattner et al. '275 further describes that it is to be understood that the physiological function of augmenting the respiratory function of this embodiment of Lattner et al. '275 contemplates stimulating portions of the vestibular system before the vestibular nerve or nerve branches to induce a neural transmission therein. Thus, this embodiment of Lattner et al. '275 also contemplates stimulating the structures of the vestibular system, such as the semicircular canals 46*a*, ampullae 46*b*, utricle 46*c*, saccule 46*d*, and common membranous limb 46*e* using any of the described stimulation mechanisms. In addition, Lattner et al. '275 contemplates globally stimulating the vestibular area in synchronization with breathing to augment the patient's respiratory function.

FIG. 1B is a perspective view of the labyrinth and associated nerves of prior art alternative embodiment for vestibular stimulation as described in the '275 patent to Lattner et al. (See Lattner et al. '275 patent FIG. 8 and associated written description). Lattner et al. '275 (see column 16, lines 13-45) describes that, in one embodiment, the sensation of rocking is induced by stimulating one or more of the semicircular canals, saccules, and/or utricles. The Lattner et al. '275 FIG. 1B example illustrates vestibular nerve 42, branch nerves 44, and vestibular ganglion 41. Also illustrated are first stimulation element 88 provided at a first location on semicircular canal 90, and a second stimulation element 92 provided at a second location on the same semicircular canal. The first and second stimulation elements 88 and 92 are operatively coupled to a signal receiving device for controlling the application of stimulation to semicircular canal 90. In one Lattner et al. '275 embodiment, stimulation elements 88 and 92 are electrodes, such as cuff electrodes, for providing electrical energy to the patient from a source. Leads 94 and 96 couple the electrodes to the power supply.

Lattner et al. '275 describes in another embodiment, first and second stimulation elements 88 and 92 are pressure-application devices, such as the pressure cuffs, that apply a pressure to the semicircular canal. In which case, leads 94 and 96 are conduits for carrying an inflating fluid to the pressure cuffs. In yet another Lattner et al. '275 embodiment, first and second stimulation elements 88 and 92 are pressure application devices located within the semicircular canal for moving the fluid contained therein. In still another embodiment of Lattner et al. '275, stimulation of the canals is accomplished via one or more vibrating elements located proximate to the semicircular canal, such as in the bone tissue adjacent the duct in which the semicircular canal is located.

In this embodiment of Lattner et al. '275, a rocking sensation is induced in the patient by alternatively actuating first and second stimulation elements 88 and 92. For example, if first and second stimulation elements 88 and 92 are pressure cuffs, first stimulation element 88 is actuated and second stimulation element 92 is deactivated to tend to urge the fluid within semicircular canal 90 in a first direction toward the second stimulation element, as indicated by arrow B. Thereafter, first stimulation element 88 is deactivated and second stimulation element 92 is actuated to urge the fluid in the opposite direction back toward the first stimulation element, as indicated by arrow C. This process is repeated to move the fluid back and forth within the semicircular canal, which is the same effect that takes place when the person is physically rocked. Lattner et al. '275 describes the frequency of the back and forth movement of the fluid can be altered to change the rocking speed of the patient.

Lattner et al. '275 describes that the placement of first and second stimulation element 88 and 92 on semicircular canal 90, which is the posterior semicircular canal, may not be the optimum location for all patients, so Lattner et al. '275 contemplates locating the first and second stimulation element on other semicircular canals, such as anterior semicircular canal 98 and/or lateral semicircular canal 100. Lattner et al. '275 describes that such stimulation elements can be provided at one or more of these semicircular canals, which is especially important given the three-dimensional nature of the human balancing system. Lattner et al. '275 further describes that the number of stimulation elements and their specific location on the associated semicircular canals is also subject to variation so long as the actuation of these stimulation elements produces a rocking sensation in the patient.

In another embodiment of Lattner et al. '275, the stimulation elements are provided at ampullae 102, saccule 104, and/or utricle 106 rather than on, in or adjacent to the semicircular canals. Lattner et al. '275 contemplates using the stimulation techniques discussed to alternatively stimulate these structures to create a rocking sensation.

In contrast, the present invention is directed to stimulation of the vestibular organs to improve balance and/or treat other conditions.

U.S. Pat. No. 7,004,645 issued to Lemoff et al. on Feb. 28, 2006, and titled "VCSEL array configuration for a parallel WDM transmitter", is incorporated herein by reference. Lemoff et al. describe VCSEL array configurations. Transmitters that use several wavelengths of VCSELs are built up out of multiple die (e.g., ones having two-dimensional single-wavelength monolithic VCSEL arrays) to avoid the difficulty of manufacturing monolithic arrays of VCSELs with different optical wavelengths. VCSEL configurations are laid out to insure that VCSELs of different wavelengths that destined for the same waveguide are close together.

U.S. Pat. No. 7,116,886 issued to Colgan et al. on Oct. 3, 2006, and titled "Devices and methods for side-coupling optical fibers to optoelectronic components", is incorporated herein by reference. Colgan et al. describe optical devices and methods for mounting optical fibers and for side-coupling light between optical fibers and VCSEL arrays using a modified silicon V-groove, or silicon V-groove array, wherein V-grooves, which are designed for precisely aligning/spacing optical fibers, are "recessed" below the surface of the silicon. Optical fibers can be recessed below the surface of the silicon substrate such that a precisely controlled portion of the cladding layer extending above the silicon surface can be removed (lapped). With the cladding layer removed, the separation between the fiber core(s) and optoelectronic device(s) can be reduced resulting in improved optical coupling when the optical fiber silicon array is connected to, e.g., a VCSEL array.

U.S. Pat. No. 7,031,363 issued to Biard et al. on Apr. 18, 2006, and titled "Long wavelength VCSEL device processing", is incorporated herein by reference. Biard et al. describe a process for making a laser structure such as a vertical cavity surface emitting laser (VCSEL). The VCSEL designs described include those applicable to the 1200 to 1800 nm wavelength range U.S. Pat. No. 6,546,291 issued to Merfeld et al. on Apr. 8, 2003, and titled "Balance Prosthesis", is incorporated herein by reference. Merfeld et al. describe a wearable balance prosthesis that provides information indicative of a wearer's spatial orientation. The balance prosthesis includes a motion-sensing system to be worn by the wearer and a signal processor in communication with the motion-sensing system. The signal processor provides an orientation signal to an encoder. The encoder generates a feedback signal on the basis of the estimate of the spatial orientation provides that signal to a stimulator coupled to the wearer's nervous system.

Vestibular problems in the inner ear, the semicircular canal organs or the otolith organs can cause very debilitating conditions, including dizziness and vertigo. Improved apparatus and methods are needed to treat various vestibular problems.

BRIEF SUMMARY OF THE INVENTION

The present invention includes a vestibular implant to deliver optical (e.g., using infrared light from a laser) stimulation of vestibular nerves in order to restore the vestibular function and improve balance and/or avoid dizziness or improve other functions of the vestibular system (i.e., eye movements, posture, gait, sleep, etc). The infrared-light nerve-stimulation technique is significant since, unlike electrical nerve stimulation, the light can selectively stimulate certain vestibular nerves without simultaneously spreading the stimulation to other sets of vestibular nerves. In some embodiments, the device has as few as five (5) channels to control the three (3) rotational vestibular sensors (i.e., to stimulate nerves of the semicircular canals) and the two (2) linear vestibular sensors (i.e., to stimulate nerves of the otolith organs—the utricle and saccule). In some embodiments, the device has as few as one (1) channel to control a single malfunctioning vestibular organ such as one of the three (3) rotational vestibular sensors (i.e., to stimulate nerves of the semicircular canals) or one of the two (2) linear vestibular sensors (i.e., to stimulate nerves of the otolith organs—the utricle or saccule). In some other embodiments, numerous channels are implanted to stimulate the vestibular sensors and/or nerves. Optical stimulators are advantageous in that a large number of stimulators can be combined into a small cross-sectional area, e.g., an optical fiber bundle, or a vertical-cavity surface-emitting-laser (VCSEL) array or other optimized and compact light source. Using a large number of optical stimulators provides easier implantation due to less critical placement of the simulators, and later testing of the implanted stimulators can determine which stimulators are most effective for stimulating the desired nerve(s) and treating the desired condition. In addition, in some embodiments, the technique of varying the wavelength is used to control the penetration depth of the nerve stimulator, which is used to externally stimulate the vestibular organs without having to physically penetrate the organs. In some embodiments, the optical stimulator is placed external to the organ and provides optical stimulation to the nerves from the organ, instead of implanting a probe (e.g., an electrical probe) internal to the organ. This is advantageous in that a less invasive surgery can be used. Further, an implantable device held within the patient's body reduces the risk of infections and other complications. In some embodiments, optical nerve stimulation is propagated through at least some amount of bone. In some other embodiments, a small hole is made into or through the bone of the skull to permit optical stimulation to the target nerves. In some embodiments, the Cranial Nerve VIII (CN VIII)—also called the vestibulocochlear nerve—is stimulated by a prosthetic device of the present invention. Some embodiments provide a vestibular prosthesis that uses surface stimulation or intrafascicular stimulation (i.e., located or occurring within a vascular bundle; e.g., some embodiments embed the optical (or electro-optical) probe fiber(s) under the collagenous layers of nerve and situate the stimulation probe on the excitable axonal layer).

In some embodiments, various laser technologies are used to provide the optical nerve stimulation. In some embodiments, a semiconductor diode laser is used. In some embodiments, a fiber laser is used. In some embodiments, a vertical-cavity surface-emitting-laser (VCSEL) array stimulator apparatus is used to provide optical nerve stimulation. In some embodiments, the laser light is delivered to the stimulation site using an optical fiber.

As used herein, a probe is the optical delivery device. In some embodiments, various probe designs are used to deliver optical stimulation to the desired area. In some embodiments, an end-emitting is used, while in other embodiments, an edge-emitting probe is used. In some embodiments, the probe has a broad emission if a large area requires activation. In some embodiments, a grating or lens in an optical fiber is used to provide a broad emission area.

In some embodiments, the optical stimulator (e.g., VCSEL array) is implanted locally or proximally to the nerves to be stimulated. In some other embodiments, the optical stimulators are remotely located and are operatively connected using optical fibers with one end implanted proximal to the nerves to be stimulated. In some other embodiments, the optical stimulators are remotely located outside the body and are operatively connected through the skin using optical fibers with one end implanted proximal to the nerves to be stimulated. In some embodiments a lens or set of lenses is used to shape the beam and direct light from the source directly to the excitable tissues.

BRIEF DESCRIPTION OF THE DRAWINGS

FIG. 3.1 is a perspective view of a conventional optical fiber array connector head 301 that is used for some embodiments of optical head 330.

FIG. 4.1 shows a conceptual view of an embodiment in accordance with the invention.

FIG. 4.2 shows an embodiment of a VCSEL array configuration 402 for a parallel wavelength-division transmitter in accordance with the invention.

FIG. 4.3 shows a simplified view of solder bumps 4199 and 4599 on the bottoms of die 4121 and die 4515, respectively.

DETAILED DESCRIPTION OF THE INVENTION

Figure 1A:
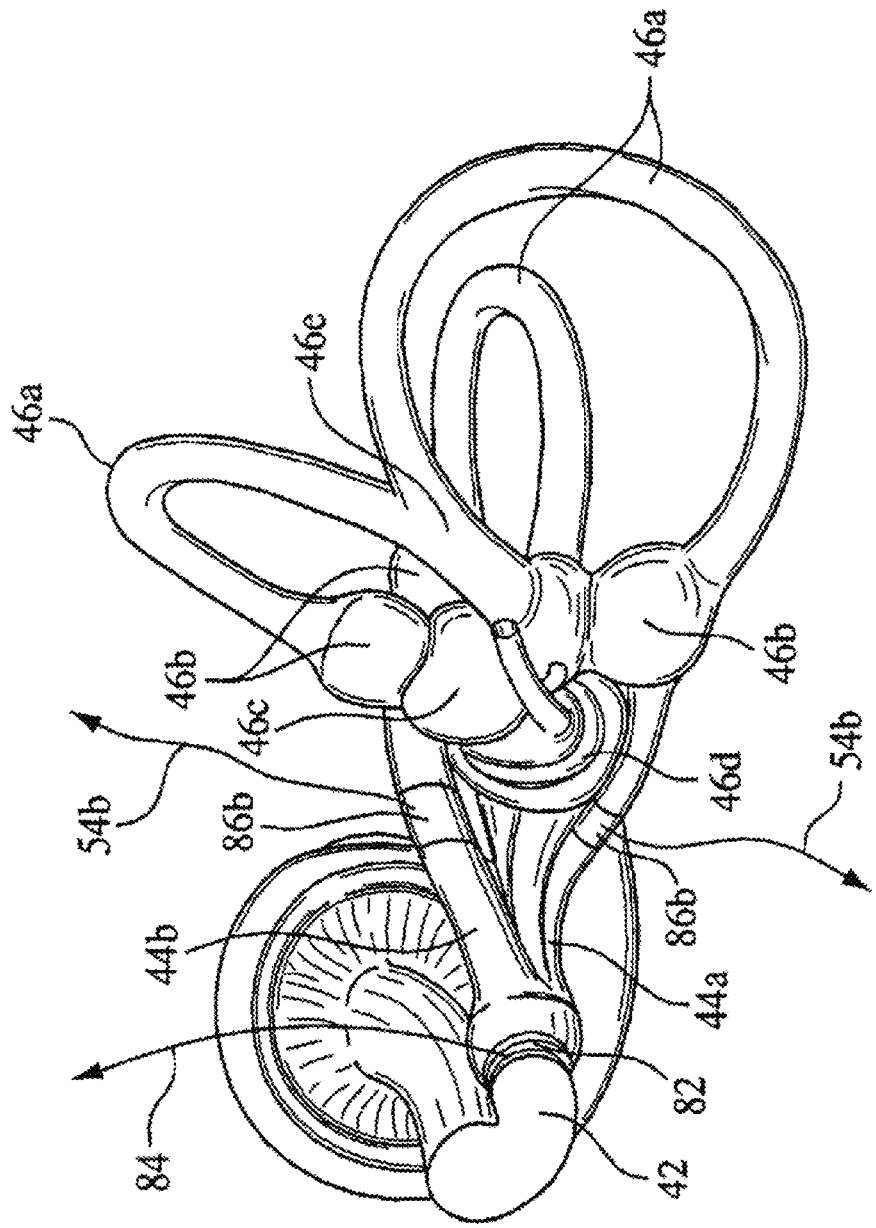
FIG. 1A is a perspective view of the labyrinth and associated nerves of prior art embodiment for vestibular stimulation.
Figure 1B:
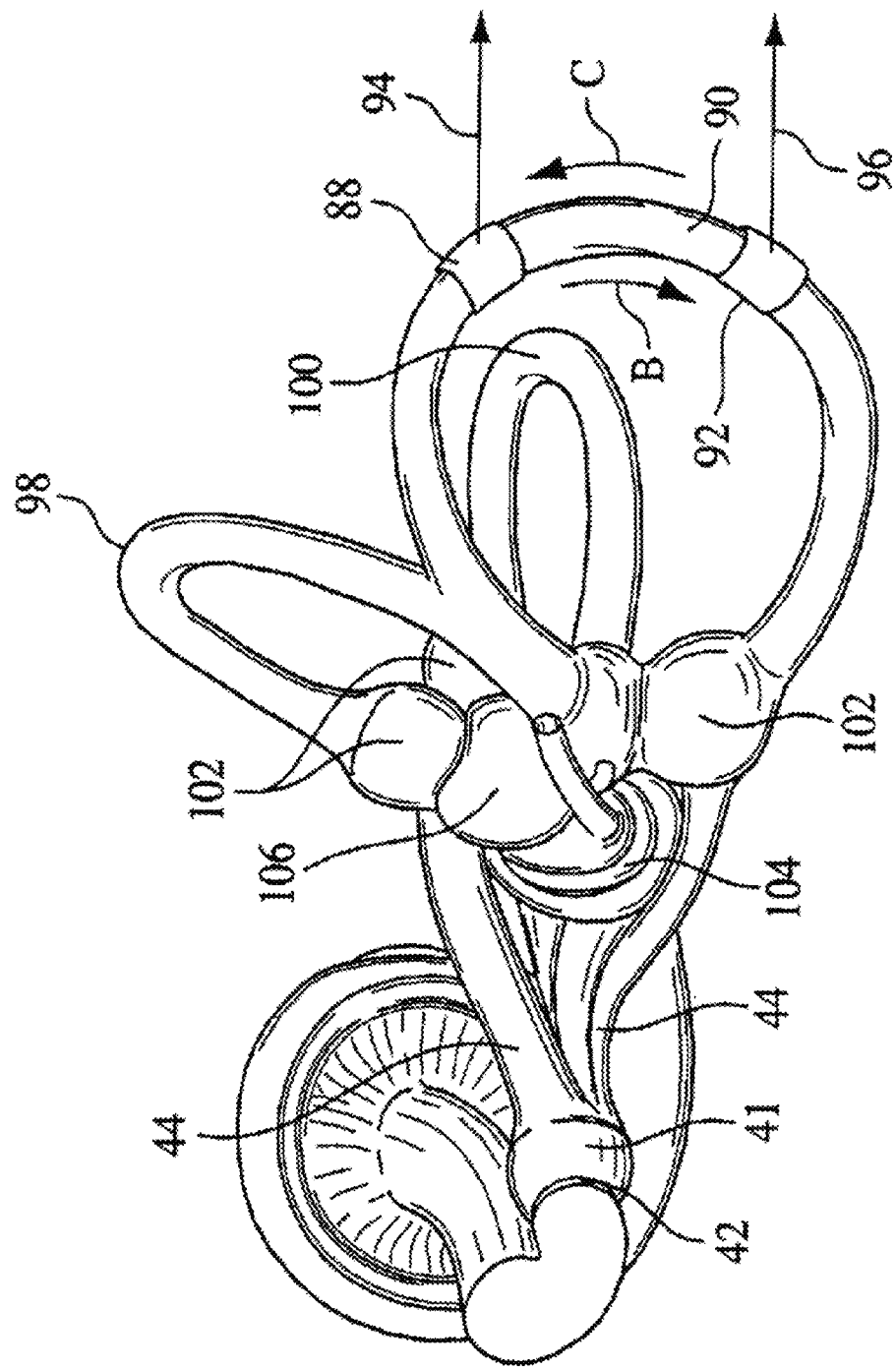
FIG. 1B is a perspective view of the labyrinth and associated nerves of prior art alternative embodiment for vestibular stimulation.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, the inner-ear vestibular organs (or vestibular organs) are defined as including the saccule and utricle otolith organs and the semicircular canal organs. As used herein, optical nerve stimulation is defined as the direct stimulation of nerves or nerve endings by means of laser light. Optical nerve stimulation includes optically stimulating nerves and especially optically stimulating in order to generate or alter one or more nerve action potentials (NAPs). Altering a nerve action potential includes preventing a nerve action potential (NAP) that would otherwise occur and/or altering the frequency of NAPs. Compound nerve action potential (CNAP) is one form of nerve action potential (NAP). As used herein, optical nerve stimulation is not limited to stimulation of the optic nerve or retina tissues (which are related to the eye and sight). Rather, optical stimulation can be used for generating a nerve signal on virtually any nerve, since any nerve or other similar excitable tissue can be optically stimulated (which generates a short temperature transient) such that the nerve generates a nerve action potential based on the laser-tissue interaction leading to a stimulatory effect.

In some embodiments, the invention provides an optical nerve stimulation device and method that provides different nerve stimulation signals to a plurality of different vestibular nerves, including at least some of the three semicircular canal nerves and/or the two otolith organ nerves. In some embodiments, balance conditions of the person are sensed by, or transmitted to, the implanted device, and based on the device-sensed balance conditions, controlled and varying optical nerve-stimulation signals are sent to a plurality of the different vestibular nerves.

An afferent nerve carries impulses (i.e., nerve action potentials) toward the central nervous system. The opposite of afferent is efferent, wherein efferent nerves carry impulses (i.e., nerve action potentials) from the central nervous system, typically to control or actuate muscles, effector organs, or glands. For at least some vestibular organs, the afferent nerves from vestibular sense organ(s) are in pairs (one on each side of the head—i.e., right and left), and when in balance, both nerves send nerve pulses at equal rates (e.g., 50 pulses per second from one of the pair of nerves and 50 pulses per second from the other), but when out of balance, send nerve pulses at different rates (e.g., 10 pulses per second from one of the pair of nerves and 90 pulses per second from the other). Thus, too few nerve pulses or too many nerve pulses can both cause a sense of imbalance. Some embodiments of the present invention provide optical nerve stimulation to cause more pulses per second to be transmitted. Some embodiments of the present invention optionally provide different optical nerve stimulation to cause fewer pulses per second to be transmitted. In some embodiments, the present invention provides an implanted stimulation device that provides vestibular stimulation to only a single side, while other embodiments provide controlled vestibular stimulation to vestibular organs on both left and right sides of a person, which can be stimulated independently, or stimulated simultaneously but at different pulse rates in order, for example, to achieve controlled differential stimulation to obtain a better sense of balance, or by other simultaneous signals to achieve a desired sensation for the patient.

Figure 2:
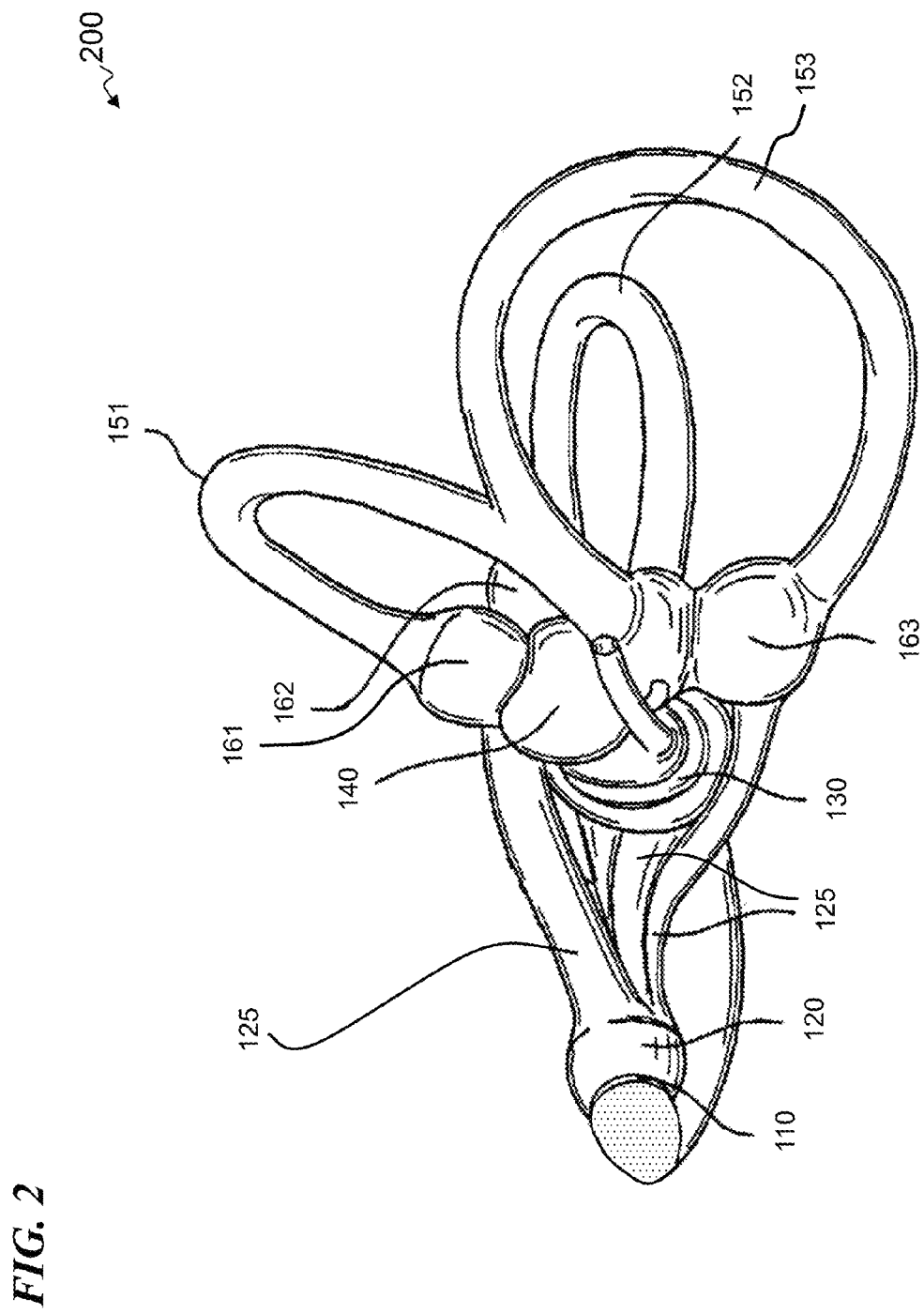
FIG. 2 is a perspective view of an inner-ear labyrinth vestibular nerves and organs 200.

FIG. 2 is a perspective view of an inner-ear labyrinth vestibular nerves and organs 200. The vestibular nerve 110 is an afferent nerve that carries impulses toward the central nervous system. The vestibular nerve branches 125 (including the anterior canal nerve, the posterior canal nerve, the lateral canal nerve, the utricular nerve, and the saccular nerve) join together at the vestibular ganglion 120. The vestibular labyrinth includes the anterior semicircular canal 151 and anterior semicircular ampulla 161, lateral semicircular canal 152 and lateral semicircular ampulla 162, posterior semicircular canal 153 and posterior semicircular ampulla 163, the utricle 140, and the saccule 130. The cochlear labyrinth includes the cochlea 180 and the cochlear nerve 170.

Figure 3:
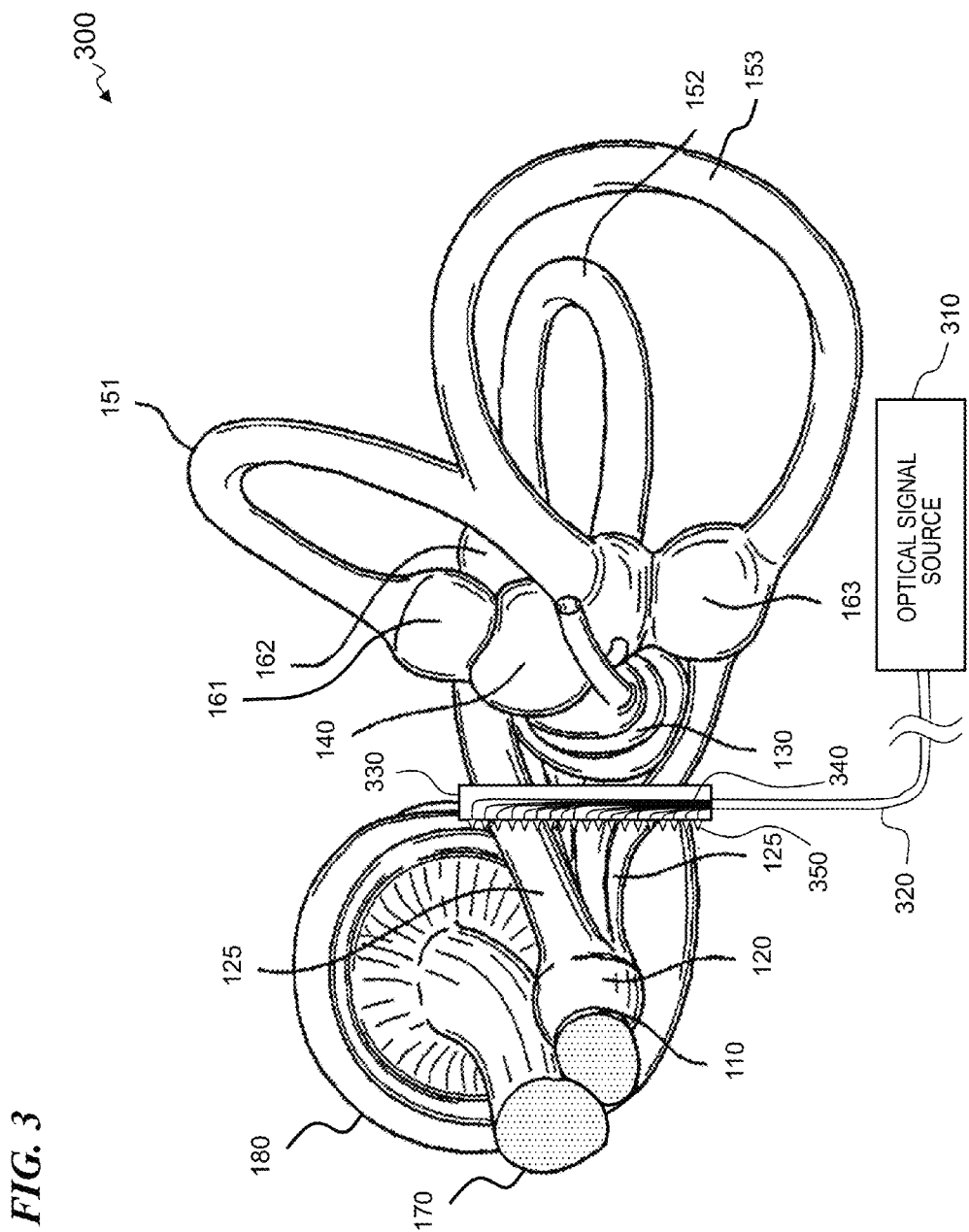
FIG. 3 is a perspective view of an inner-ear labyrinth and one embodiment of the present invention using optical sources and optical fiber(s) to provide optical stimulation to vestibular nerves.

FIG. 3 is a perspective view of an inner-ear labyrinth and one embodiment of the present invention using an optical signal source and optical fiber to provide optical stimulation to vestibular nerves. In some embodiments, an optical signal source 310 (such as a VCSEL array or a plurality of VCSEL sources) provides a plurality of light signals from one or more laser light sources. Optical fiber bundle 320 carries the light signals from the optical signal source 310 to the optical head 330. The optical head 330 routes the optical fibers 340 of the optical bundle 320 to a plurality of optical lenses 350. In the embodiment shown, the optical lenses 350 direct the light signals from the optical signal source 310 toward the vestibular nerve branches 125. In some other embodiments, the optical lenses 350 direct the light signals from the optical signal source 310 toward the vestibular nerve 110. In some other embodiments, the optical lenses direct the light signals from the optical source 310 toward one or more nerves of the vestibular ampullae 161, 162, 163, utricle 140, and the saccule 130.

In some embodiments, fiber-optic connection and delivery configurations, long-wavelength VCSEL devices, and VCSEL arrays, such as described in U.S. Pat. No. 7,116,886, U.S. Pat. No. 7,031,363 and U.S. Pat. No. 7,004,645 (which are each incorporated herein by reference), are used for the optical fiber bundle 320 and optical signal source 310.

FIG. 3.1 is a perspective view of a conventional optical fiber array connector head 301 that is used for some embodiments of optical head 330. The connector 301 comprises two plates 311 and 312 (e.g., silicon plates) each having an array of optical fiber support channels 311a, 312a (V-grooves) formed on interior surfaces thereof, corresponding to a longitudinal direction of optical fibers to be mounted therein. A plurality of optical fibers 313 are secured in corresponding channels 311a, 312a, between the plates 311, 312 using known clamping and bonding methods. The FIG. 3.1 shows that the light-emitting front face 319 is planar and the light is emitted in substantially parallel directions from the plurality of fibers 313 at that front face 319.

In general, an optical-fiber-connector head such as shown in FIG. 3.1 based on a silicon V-groove array is formed by: (1) etching V-groove channels into a silicon substrate and dicing silicon plates (having the channels) out from the wafer; (2) bonding the optical fiber(s) between corresponding V-grooves of top and bottom plates; and then (3) grinding and polishing the mating end of the connector so that the ends of the optical fiber(s) are coplanar with the front face 319 at the front edges of the V-groove plates 311, 312. For an optical-fiber-connector head that will not be permanently joined with an index matching material, it is desirable to have the optical fibers project slightly beyond the edges of the V-groove plates to ensure that there is no gap between the connected optical fibers. Silicon V-channel arrays are preferably employed for forming silicon spacing chips and connectors such as shown in FIG. 3.1 because the silicon v-groove arrays can be readily fabricated with high precision via anisotropic etching of single crystalline silicon. More specifically, the formation of V-grooves in silicon is based on knowledge that the crystal of the silicon wafer has different atomic densities-per-unit-area on different surfaces (silicon crystal-lattice orientations commonly known as 100, 110, 111) of the crystal lattice, and that the etching rates vary along the different directions of the crystal lattice. Further, silicon is a very rigid material with a low thermal coefficient of expansion, which properties render silicon ideal for mounting optical fibers.

Figure 4:
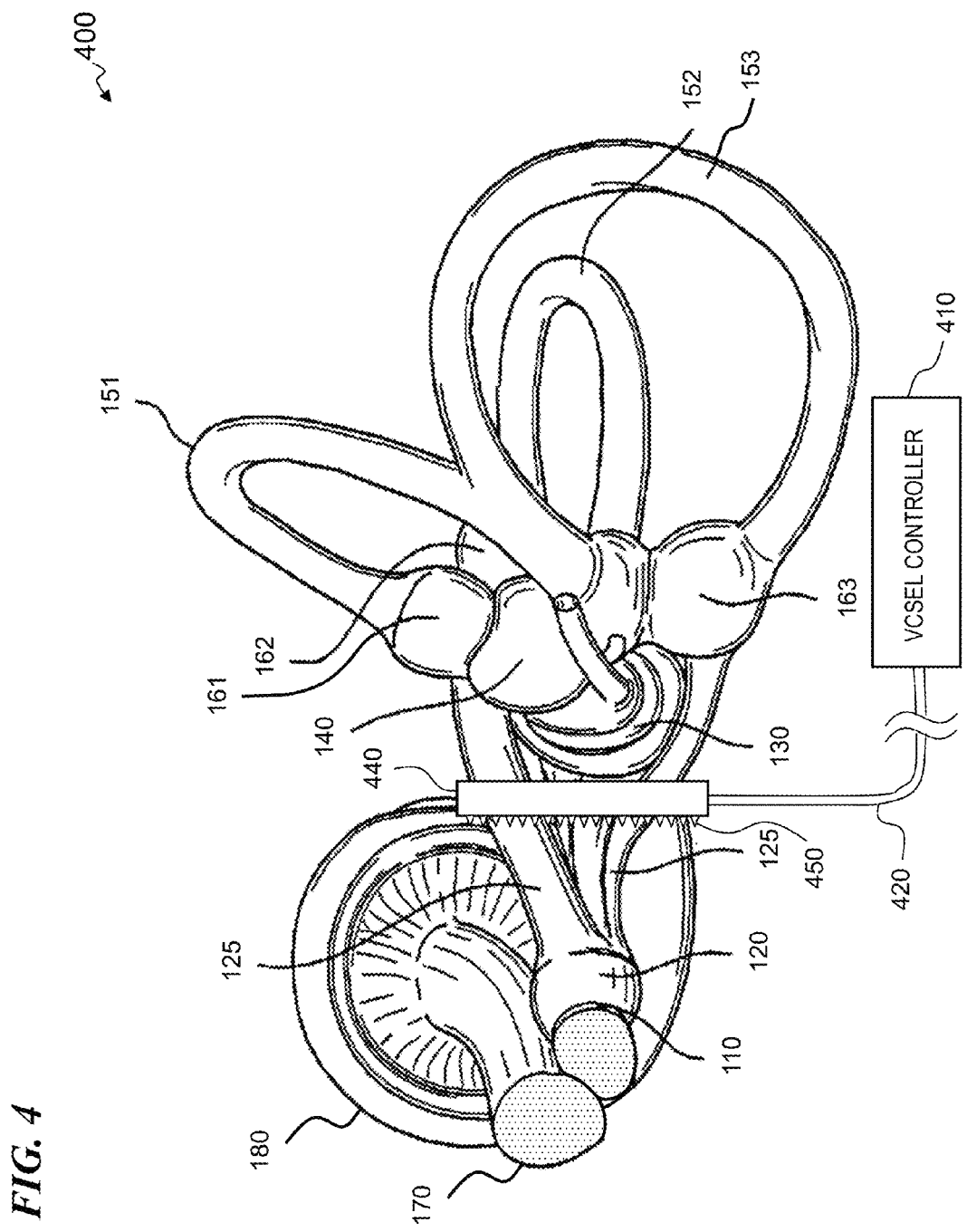
FIG. 4 is a perspective view of an inner-ear labyrinth and one embodiment of the present invention using a VCSEL controller and VCSEL array to provide optical stimulation to vestibular nerves.

FIG. 4 is a perspective view of an inner-ear labyrinth and one embodiment of the present invention using a VCSEL controller and VCSEL array to provide optical stimulation to vestibular nerves. In some embodiments, a VCSEL controller 410 provides a plurality of electrical signals and is operatively connected to the VCSEL array head 430 through electrical bundle 420. The electrical signals drive a VCSEL array head 430 implanted near the vestibular organs producing light signals. The VCSEL array head 430 produces a plurality of laser light signals. In some embodiments, the VCSEL array head 430 contains a plurality of optical lenses 450 to direct the laser light on to the nerves and/or tissue. In the embodiment shown, the optical lenses 450 direct the light signals from the VCSEL array head 440 toward the vestibular nerve branches 125. In some other embodiments, the optical lenses 450 direct the light signals from the VCSEL array head 430 toward the vestibular nerve 110. In some other embodiments, the optical lenses direct the light signals from the VCSEL array head 440 toward one or more nerves of the vestibular ampullae 161, 162, 163, utricle 140, and the saccule 130.

In some embodiments, long-wavelength VCSEL devices and/or VCSEL arrays, such as described in U.S. Pat. No. 7,031,363 and U.S. Pat. No. 7,004,645 (which are each incorporated herein by reference), are used for the VCSEL array head 440 in FIG. 4.

In accordance with the invention, a configuration of VCSELs may be arranged as linear arrays, N-by-N arrays or other geometries in accordance with the invention. FIG. 4.1 shows a conceptual view of an embodiment in accordance with the invention. In some embodiments, each of the VCSELs 4100, 4200, 4300, 4400 operates at a separate wavelength to generate light beams 460, 461, 462, 463, each light beam being at a particular wavelength. Filterless parallel wavelength-division multiplexer element 401 is used to direct light, from VCSEL configuration 470, comprising VCSELs 4100, 4200, 4300, 4400, to the destination target 425. The number of VCSELs and lenses may be increased along with the number of optical targets. Using two or more filterless parallel wavelength-division multiplexer elements 401 with two or more optical destination targets, respectively, results in a filterless parallel wavelength-division multiplexer.

Lenses in plane 4001, such as lenses 411, 421, 431, 441, are typically made just large enough to collect most of the light emitted by VCSELs 4100, 4200, 4300, 4400 such as beams 460, 461, 462, 463, respectively. The general design considerations are as follows. Because a VCSEL typically emits a vertical cone of light, the center of the lens aperture in plane 4001 should be aligned with the VCSEL aperture to capture the VCSEL light. In order to direct light from a first lens in a first plane to the appropriate lens in a second plane, the vertex of the first lens must lie on the line connecting the VCSEL aperture to the center of the appropriate lens aperture in the second plane. This results in an offset between the center of the first lens aperture and the vertex of the first lens. Therefore, the first lens is an off-axis section of a lens. The appropriate lens in the second plane needs to be large enough to capture most of the light incident on it and focus this light into the optical destination target. The lens in the second plane focuses the incident light into the optical fiber which is positioned to minimize the overall range of angles of the incident light going into the optical destination target. Because the lens in the second plane needs to focus the incident into the optical destination target, the line connecting the optical destination target center with the lens vertex needs to be parallel to the incident light which by design is parallel to the line connecting the VCSEL aperture to the center of the lens in second plane. This requires that there be an offset between the center of the lens aperture in the second plane and the lens vertex. Hence, the lens in second plane is also off-axis. The other lenses of the multiplexer and any additional optical destination targets are similarly positioned.

The general design considerations discussed above assume that the VCSEL is a point source, which is an approximation. Additional assumptions have neglected diffraction and lens aberrations. The design implementation of wavelength-division multiplexer 401 corrects for these factors and the implementation typically will differ from the above description that, however, results in a baseline design that is qualitatively similar to the actual implementation. In practice, the qualitative description provides a starting configuration that may be iteratively modified using ray-tracing software packages such as ZEMAX® or CODE V® until the amount of VCSEL light reaching the optical fiber has been optimized.

With respect to FIG. 4.1, for example, VCSEL 4100 is lined up with the center of lens 411, and lens 411 needs to be large enough to capture most of the light from VCSEL 4100. The vertex of lens 411 lies in plane 4001 on the line defined by VCSEL 4100 and the center of lens 412. Hence, the vertex of lens 411 and the center of the aperture of lens 411 are offset from each other and lens 411 is an off-axis lens. Lens 412 in plane 4002 needs to be sufficiently large to collect most of the light incident on it and focus that light into destination target 425. Lens 412 focuses most of the incident light into destination target 425 which is positioned to minimize the overall range of angles of the incident light that is entering destination target 425. Because lens 412 focuses the light into destination target 425, the line connecting the center of destination target 425 needs to be parallel to the incident light. By design, the incident light is parallel to the line connecting the aperture of VCSEL 4100 to the center of lens 412 in plane 4002. This requires that the vertex of lens 412 and the center of the aperture of lens 412 are offset from each other. Hence, lens 412 is also an off-axis lens. Similar considerations apply for lenses 421, 431, 441 in plane 4001 and lenses 422, 432, 442 in plane 4002.

As described above, in some embodiments, each of VCSELs 4100, 4200, 4300, 4400 operates at a separate wavelength to generate light beams 460, 461, 462, 463, each light beam being at a particular wavelength. VCSELs 4100, 4200, 4300, 4400 typically reside on separate die. Light beams 460, 461, 462, 463 enter filterless parallel wavelength-division multiplexer 401 having two planes of lenses. In FIG. 4.1, VCSELs 4100, 4200, 4300, 4400 transmit light beams 460, 461, 462, 463 to lenses 411, 421, 431, 441 residing in first lens plane 4001. Lenses 411, 421, 431, 441 function to redirect beams 460, 461, 462, 463 into lenses 412, 422, 432, 442, respectively. Lenses 412, 422, 432, 442 residing in second lens plane 4002 function to direct light beams 460, 461, 462, 463, respectively, into destination target 425. Hence, light of four different wavelengths is multiplexed into destination target 425.

FIG. 4.2 shows an embodiment of a VCSEL array configuration 402 for a parallel wavelength-division transmitter in accordance with the invention. Configuration 402 shown in FIG. 4.2 is a four-wavelength, twelve-destination-target configuration constructed from two-dimensional single-wavelength monolithic VCSEL arrays. In this embodiment, there are three groups 4101, 4102, 4103 of four square dies 4121, 4122, 4123, 4124 corresponding to two-by-two VCSEL arrays 4150, 4160, 4170, 4180, respectively. The number of dies and groups in the configuration may be increased in accordance with the invention to allow for both more wavelengths and destination targets. VCSEL arrays 4150, 4160, 4170, 4180 each operate at a different wavelength. Dies 4121, 4122, 4123, 4124 are arranged such that each group 4101, 4102, 4103 contains VCSEL arrays for each of the four wavelengths. This arrangement ensures that devices of different wavelengths are sufficiently close together to avoid the need for large angle deflections within multiplexer element 401 (i.e., between planes 4001 and 4002) to direct the light beams into each respective destination target 425. The need for large angle deflections using refractive lenses presents a cost issue and using diffractive lenses results in higher light losses.

The substantially square aspect ratio of dies 4121, 4122, 4123, 4124 improves handle-ability in the manufacturing environment and reduces handling breakage. VCSEL material is typically brittle and VCSEL structures with a high aspect ratio are inherently more susceptible to damage than VCSEL structures with a low aspect ratio. Long VCSEL arrays (high aspect ratio) have proportionally more surface area than square VCSEL arrays (low aspect ratio). For example, a three-by-three VCSEL array on a 250-µm pitch has nine devices with a perimeter of 3000 µm whereas a one-by-nine VCSEL array also has nine devices but for the same pitch has a 5000-µm perimeter. Because cracks usually start on the die perimeter, reducing the die perimeter typically increases the VCSEL-array yield. Additionally, long VCSEL arrays are typically subject to more stress due to thermally induced stresses resulting from attachment to the substrate material.

Conventional production tooling is typically designed to handle parts that have a low aspect ratio. The majority of semiconductor devices have a relatively low aspect ratio (typically an approximately square shape when viewed from the top or bottom) and as a result, the conventional production tooling is typically designed to accommodate such low aspect ratio shapes.

Using two-by-two VCSEL arrays 4150, 4160, 4170, 4180 located on dies 4121, 4122, 4123, 4124, respectively, the arrangement of the bond-pads (not shown) on each die 4121, 4122, 4123, 4124 allows the use of solder-reflow self alignment during alignment and attachment, decreasing assembly costs. Typically, solder-reflow self alignment is more effective for two-by-two arrays such as VCSEL arrays 4150, 4160, 4170, 4180.

FIG. 4.3 shows a simplified view of solder bumps 4199 and 4599 on the bottoms of die 4121 and die 4515, respectively. Solder bumps 4199 and 4599 act to self align die 4121 and die 4515, respectively, during reflow.

The self-alignment mechanism is due to minimization of the surface tension at each of the individual solder attachment sites so that at each solder attachment site the surface tension is minimized. Each solder bump has a somewhat different volume and wets the bonding pads somewhat differently. The differences are relatively small but cause each solder bump to pull dies 4121 and 4515 in a different direction. A vector summing of the various forces occurs resulting in the final positioning of die 4121 and 4515. Because a two-by-two VCSEL array has a higher degree of symmetry than a one-by-twelve VCSEL array, better alignment typically results for a two-by-two VCSEL array or other VCSEL arrays having a higher degree of symmetry than a one-by-twelve array VCSEL array.

The size of two-by-two VCSEL arrays 4150, 4160, 4170, 4180 can be reduced in size to the minimum size needed for solder bumps to attach VCSEL arrays 4150, 4160, 4170, 4180 to the substrate. For example, if sufficiently small solder bumps are used to attach two-by-two VCSEL arrays 4150, 4160, 4170, 1480 that are 150 μm on a side, the VCSEL array size will work with filterless parallel wavelength-division multiplexer even if the pitch of the optical fiber array is 250 μm. In contrast, for one-by-twelve VCSEL arrays, the pitch of the VCSEL array is constrained by and must match the pitch of the optical fiber array. Because the cost of VCSEL die is proportional to their area cost may be reduced by reducing area. In addition, having a relatively small number of devices per die increases the yield per die. For example, if 5% of the VCSELs in a one-by-twelve VCSEL arrays are defective, the array yield will be about 54% if the defects are random. For two-by-two VCSEL arrays 4150, 4160, 4170, 4180 with the same defect rate of 5%, the array yield will be 81%. Because yield per die is proportional to cost, smaller arrays are much cheaper.

Figure 5:
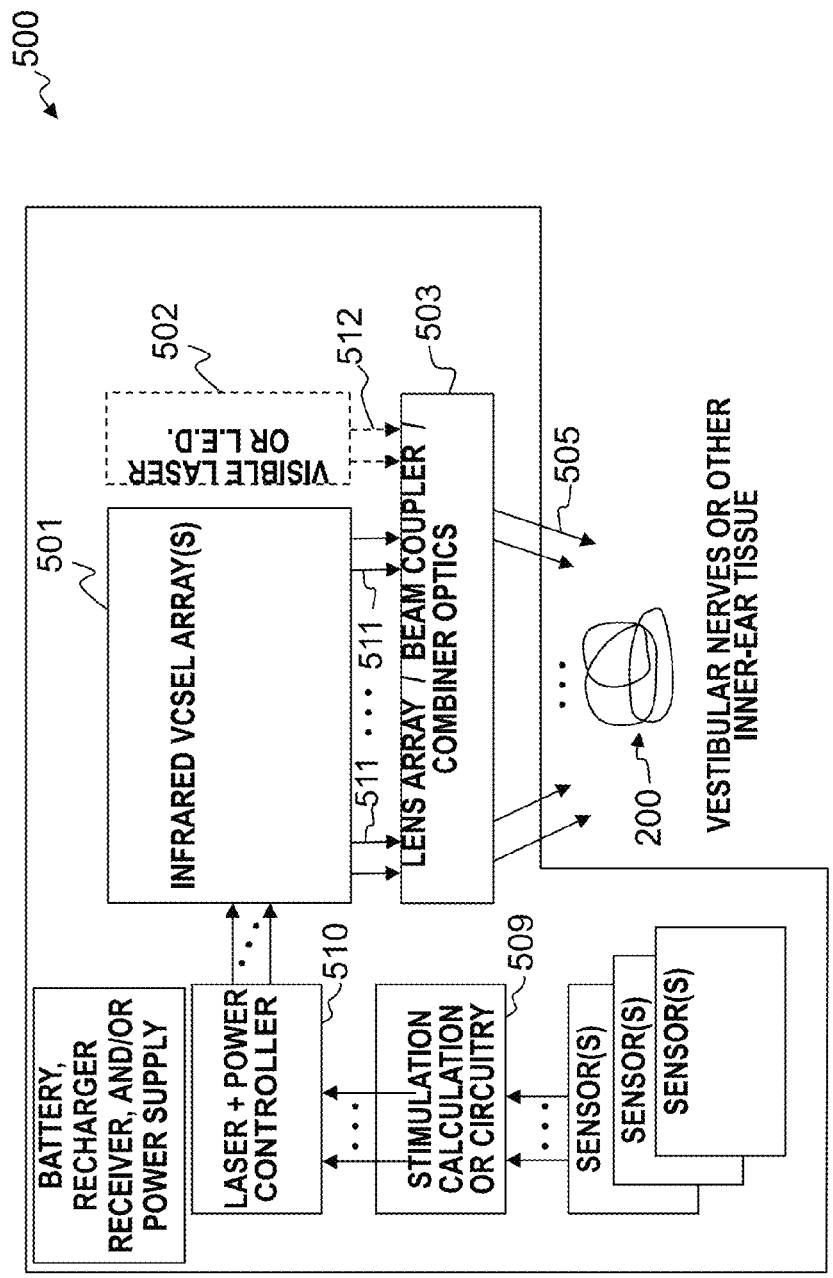
FIG. 5 is a block diagram of an implantable system 500 that uses a VCSEL array for light stimulation of vestibular nerves and/or organs 200.

FIG. 5 is a block diagram of an implantable/partially implantable system 500 that uses a VCSEL array for light stimulation of vestibular nerves and/or organs 200 (e.g., some embodiments use a VCSEL array such as described by U.S. Provisional Patent Application No. 60/964,634 filed Aug. 13, 2007, titled "VCSEL Array Stimulator Apparatus and Method for Light Stimulation of Bodily Tissues"). System 500 represents one embodiment of the present invention, wherein a low-power, low-threshold VCSEL array 501 emits laser light from each of a plurality of VCSELs, for example VCSELs implemented as an array of separately activatable lasers formed in a monolithic semiconductor chip. Each laser beam is separately controlled by laser-and-power controller 510 that drives the laser-diode VCSELs under control of a processor or circuitry 509 that generates signals that are configured to stimulate the tissue as desired. For example, in some embodiments, the light signals 505 are collimated, focused and/or guided by optics 503. In some embodiments, the system uses a visible laser and/or LED array 502 that produce visible light signals 512 to help align the VCSEL laser array signals 511 with the lens array/beam coupler/combiner optics 503.

In some embodiments, long-wavelength VCSEL devices and/or VCSEL arrays, such as described in U.S. Pat. No. 7,031,363 and U.S. Pat. No. 7,004,645 (which are each incorporated herein by reference), are used for the VCSEL array 501.

With VCSEL emitters as small as about ten (10) microns (or smaller) in diameter per channel, in some embodiments, a single VCSEL chip or assembly is used to output multiple independent stimulation channels (VCSEL laser signals) in any array permutation or shape, and in some embodiments, these channels are fiber coupled and/or direct light straight to a plurality of areas of tissue. In some embodiments, a combination of both fiber-coupled and direct propagation laser output is used to stimulate tissue.

Figure 6:
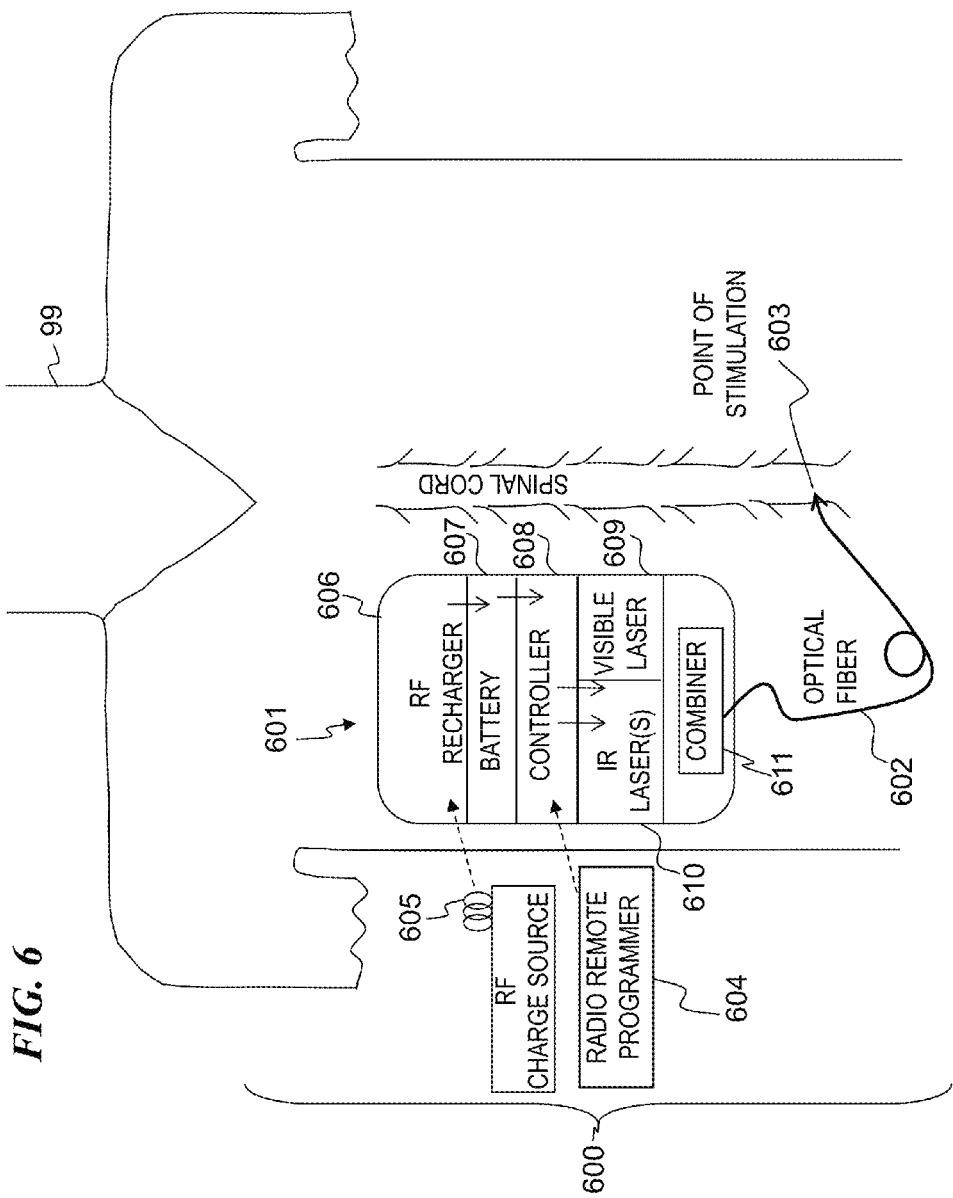
FIG. 6 is a schematic 600 detailing an implantable version of a device that is powered and controlled via an external source.

FIG. 6 is a schematic 600 detailing an implantable version of a device that is powered and controlled via an external source. In some embodiments, an optical stimulator 601 is implanted into a subject (e.g., a patient) 99 to provide an efficacious amount of IR-light stimulation to a nerve fiber. In some embodiments, this optical stimulator 601 contains components including an RF recharger 606, battery 607, controller 608, visible-laser source 609, IR-laser source 610 and combiner 611, with each being operatively coupled to each other such that the RF recharger 606 provides electrical power to the battery 607, which, in turn powers the controller 608. The controller 608 provides electrical power and control signals to the visible-laser source 609 and IR-laser source 610, regulating type and intensity of pulse generated by each of these sources. In some embodiments, the light from these sources (i.e., 609 and 610) is sent to a combiner 611 where the light is combined into a single beam. In some embodiments, the combiner 611 is operatively coupled to an optical-fiber structure 602 that is then positioned such that it can deliver an efficacious amount of IR light to a point of stimulation 603. In some embodiments, this point may be nerve fibers located along the spinal cord, whereas in other embodiments this point of stimulation 603 may be some other group of nerve fibers. As with other embodiments, light from the visible-laser source 609 is used to position the optical-fiber structure 602 relative to a point of stimulation 603. Once the optical-fiber structure 602 is positioned, IR laser light may be applied.

In at least one embodiment, control of the optical stimulator 601 is via a radio remote programmer 604 that sends control signals to the above-described controller 608. In some embodiments, an RF charge source 605 is used to supply electrical power to the optical stimulator 601.

In some embodiments, a plurality of light-emitting optical-fiber structures is used to emit efficacious IR and/or visible light to stimulate nerve tissue. In at least one embodiment, the tips of these optical-fiber structures are arranged in an array-type pattern, whereas in other embodiments the tips are arranged in a matrix-type pattern. Other patterns are also provided and are only limited by empirical testing and/or modeling to determine which patterns are more or less effective.

In some embodiments, in those instances where an array- or matrix-type configuration is used software is used to isolate an isomorphism between a particular light-emitting optical-fiber structure and certain nerve tissues. Put another way, once a reaction of a particular nerve tissue is determined, software can be used to determine which light-emitting optical-fiber structure actually caused the reaction on the part of the nerve tissue. The algorithm to determine which light-emitting structure caused a reaction could be a simple sequential-search algorithm whereby each light-emitting optical-fiber structure individually emits light by itself and a nerve-tissue reaction is determined to be present or absent, or it could be a more sophisticated binary-search algorithm whereby, for example, an array of light-emitting optical-fiber structures is divided in half, each sub-array tested individually to determine whether a nerve-tissue reaction is present or absent, and if one sub-array is indeed associated with a nerve-tissue reaction then that sub-array is again divided in half and the process repeated. Some embodiments use algorithms to search array-like structures and matrices, such as are well known in the art. (See Algorithms in C++: Parts 1-4 $3^{rd}$ Edition, by Robert Sedgewick, Addison Wesley 1998.)

Figure 7:
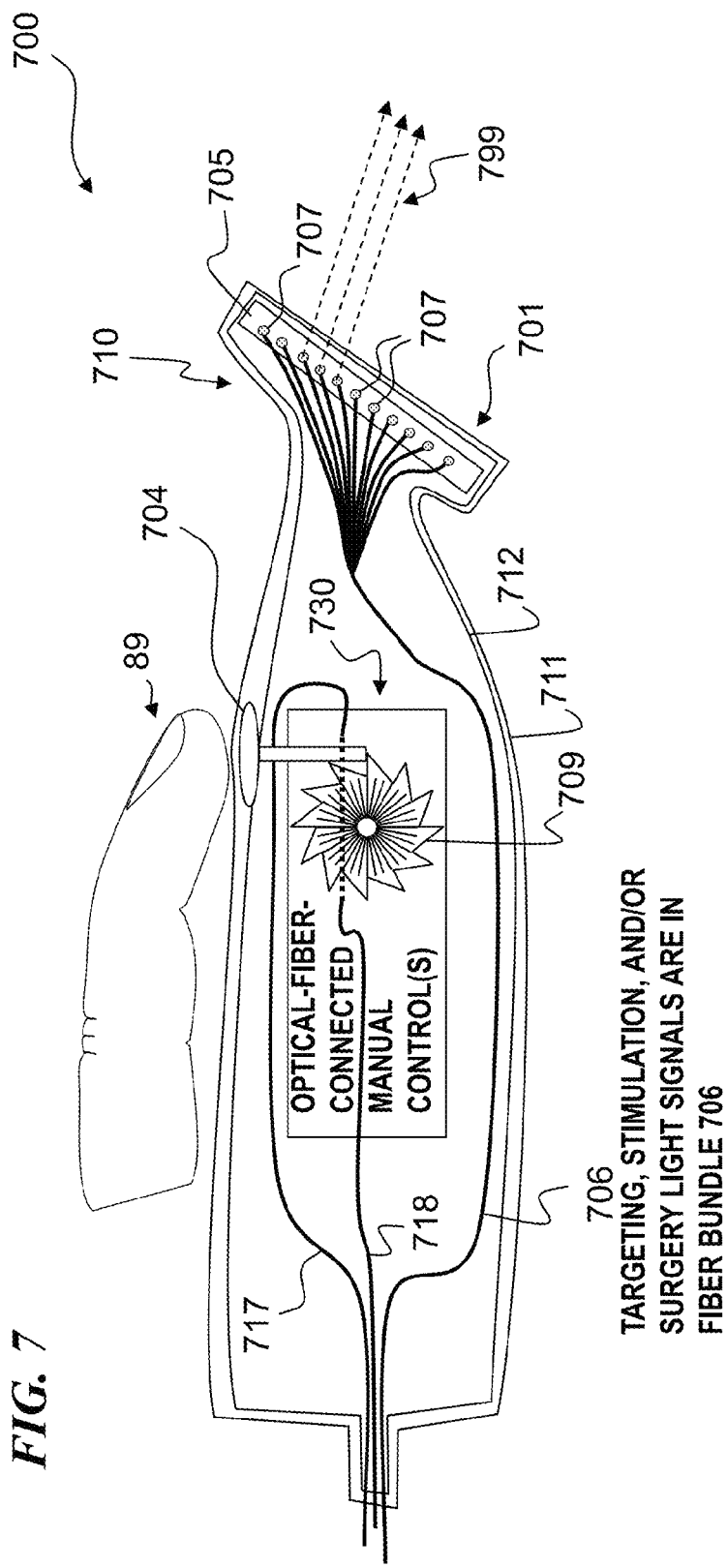
FIG. 7 is a block diagram of a light-delivery device 700 using a manually controlled selector 704 and delivery system 710 of laser light.

FIG. 7 is a block diagram of a light-delivery device 700 using a manually controlled selector 704 and delivery system 710 of laser light. In some embodiments, delivery system 710 includes a multi-fiber ferrule 705 presenting a plurality of optical-fiber-structure ends 707 closely spaced apart along a line and placed into a delivery head 701. Fiber bundle 706 includes a plurality of fibers that, in some embodiments, are each separately controllable to selectively deliver stimulation light signals to one or more of the plurality of optical-fiber-structure ends 707.

In some cases, for each fiber in bundle 706 a single-emitter diode with a single-mode fiber is used, depending on the nerve size. In some embodiments, the head 701 is placed across a nerve bundle within which the desired nerve of interest is located. Individual optical fibers of fiber bundle 706 are illuminated with stimulation light successively, in order to locate a particular nerve of interest. This allows the user to move the light beam small distances between adjacent nerves without moving the delivery head or having to manually adjust small distances by hand. In some embodiments, a foot control having the same functionality is used in place of button or lever 704 and selector wheel 709, in order that small hand movements (as might be needed to actuate button 704) do not end up moving optical delivery head 701 relative to the nerve bundle.

In some embodiments, nerve-stimulating IR light is emitted from the one or more of the plurality of optical-fiber ends 707 in a successive sequence as controlled, e.g., through the depression of a button or lever 704 by the operator's finger 89, that controls movement of ratcheting selector wheel 709, which interrupts light passing from light-source fiber 717 to light-sensor fiber 718. In some embodiments, light-source fiber 717 and light-sensor fiber 718 are used to control delivery of optical-nerve-stimulation light through the stimulation fiber 706. In some embodiments, the effectiveness of the IR-light stimulation is determined by observing muscle twitches, through the patient (or other subject) reporting a touch or other sensation, or by, for example, observing an fMRI image. In some embodiments, light delivered through fiber bundle 706 is controlled to sequentially scan the light signal 799 across head 701.

In some embodiments, the pattern and speed of scanning is predetermined by a computer program, while in other embodiments the pattern is manually controlled by operator 89. In some embodiments, the computer program controls the emission of stimulation laser light in some type of pattern based upon an algorithm (e.g., a programmed binary search, sequential search, or the like) so as to determine which optical-fiber end 707 delivered an efficacious dose of IR light to the nerve of interest. This allows placement of head 701 across a region of tissue that contains the specific nerve of interest at some unknown position, and then scanning the position of the light output to the different optical-fiber ends 707 to locate the specific nerve without further movement of head 710. In some embodiments, the algorithm includes one or more of the following: optically scanning a plurality of tissue areas, detecting a response of interest, and determining which of the scanned tissue areas, when optically stimulated, causes the response of interest. In some embodiments, the method further includes outputting visible light to point out a physical location of the scanned tissues that caused the response of interest (e.g., shining a laser light out the one fiber end 707 that would illuminate the selected nerve). In some embodiments, the algorithm includes delivering different temporal patterns and/or intensity profiles of one or more light pulses all to a single location, and then repeating this for other locations. In some embodiments, the start and/or progression of the algorithm is operator controlled (e.g., in some embodiments, a finger control such as control mechanism 730 having one or more separately activable mechanisms (e.g., buttons) 704 and one or more light-interrupter wheels 709, connected to respective optical control-signal fibers 717 and 718 of FIG. 7).

The actual reaction or response of nerve tissue to IR-light stimulation would, in some embodiments, be determined through empirical observation (muscle twitches), subject reporting (of a touch sensation, taste sensation, or other sensation), by or some other method known in the art. In some embodiments, the user changes the position and/or function (e.g., changing the pulse length or intensity) of the handpiece on the basis of the response. In other embodiments, the response is detected by the stimulation system, and the function of the stimulation system automatically adjusts the stimulation based on the response feedback (e.g., in some embodiments, a stimulation signal is repeated until the response is detected, and then the stimulation stops and/or an audio or visual indication of the response is output by the stimulation system). The manipulation of the array head itself is facilitated, in, at least one embodiment, through the use of an ergonomically designed handle 712, which is covered by a replaceable, disposable, sterile sheath 711, and by the feedback to the user provided by having visible light delivered to the area that would be stimulated by the IR stimulation signal and/or the other audio and/or visual indications.

In some embodiments, light-delivery device 700 also includes light-sensing capabilities in the same head configuration, wherein an optical-nerve-stimulation light signal is sent out one or more of the fibers and a change in the appearance of the nerve or the surrounding tissue is sensed to determine whether or not the correct nerve was selected by the stimulation signal. For example, in some embodiments, a stimulation signal is sent out a first fiber and the fibers on either side are sensed (in the visible, UV and/or IR light spectrum) to determine if the desired response occurred.

In other embodiments, light-delivery device 700 also includes light-sensing capabilities in the same head configuration, wherein an observation light signal (i.e., having one or more selected light frequencies) is sent out one or more of the fibers in bundle 706 (or, in other embodiments, ambient room illumination is used), and the color or the appearance of the nerve or the surrounding tissue is sensed through that fiber end 707 or neighboring optical fibers to determine whether the location of tissue selected by the observation signal was nerve tissue or other tissue based on differences in the color of the reflected light or other sensed. In some embodiments, a visible light is sent out on one or more of the fibers in bundle 706 to illuminate and point out to the surgeon where the nerves are located (one or more of the fiber ends 707 would illuminate just the nerve tissue without illuminating other tissue).

In some embodiments, the present invention provides a method that includes obtaining a plurality of light signals from one or more laser light sources; delivering the plurality of light signals to one or more nerves of each of one or more inner-ear vestibular organs of a living animal; and selectively controlling the plurality of light signals to optically stimulate the one or more nerves in order to control nerve action potentials (NAPS) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog, cat, rodent or the like.

In some embodiments, the selectively controlling the light signals includes controlling a pulse width of the plurality of light signals.

In some embodiments, the selectively controlling the light signals includes controlling a duty cycle of the plurality of light signals.

In some embodiments, the selectively controlling the light signals includes controlling an on-time and an off-time of the plurality of light signals.

In some embodiments, the selectively controlling the light signals includes controlling a wavelength of the plurality of light signals.

In some embodiments, the selectively controlling the light signals includes controlling a pulse repetition rate of the plurality of light signals.

In some embodiments, the selectively controlling the light signals includes controlling a pulse shape of the plurality of light signals.

In some embodiments, the selectively controlling the light signals includes controlling a minimum light intensity and a maximum light intensity of the plurality of light signals.

In some embodiments, the present invention provides a combination of electrical and optical stimulation.

In some embodiments, the selectively controlling the light signals includes controlling a DC background amount of light intensity of the plurality of light signals.

In some embodiments, the present invention provides a combination of electrical and optical stimulation. In some embodiments, the method further includes selectively controlling and applying to one or more tissues of the animal one or more electrical signals (i.e., hybrid electrical and optical stimulation of one or more tissues). In some embodiments, the selectively controlling and applying the electrical signal (s) includes controlling and applying a DC background amount of electrical signal. In some embodiments, the selectively controlling and applying the electrical signal(s) includes applying electrical pulses.

In some embodiments, the selectively controlling the light signals includes controlling a precharge amount of light intensity followed by a trigger amount of light intensity of the plurality of light signals.

In some embodiments, the selectively controlling the light signals includes controlling the light signals to delay at least some of the NAPs produced by the one or more nerves that would otherwise occur without the plurality of light signals.

In some embodiments, the selectively controlling the light signals includes controlling the light signals to increase a frequency of the NAPs produced by the one or more nerves that would otherwise occur without the plurality of light signals.

In some embodiments, the selectively controlling the light signals includes controlling the light signals to decrease a frequency of the NAPS produced by the one or more nerves that would otherwise occur without the plurality of light signals.

In some embodiments, the obtaining the plurality of light signals includes implanting a self-contained battery-powered laser-light-generation device.

In some embodiments, the plurality of light signals includes implanting self-contained infrared (IR) laser device.

In some embodiments, the delivering the plurality of light signals to one or more nerves of each of one or more inner-ear vestibular organs includes using one or more optical fibers to guide the light signals.

In some embodiments, the delivering the plurality of light signals to one or more nerves of each of one or more inner-ear vestibular organs includes positioning a delivery end of one or more fibers against a vestibular organ and using the one or more optical fibers to guide the light signals from a laser source to the vestibular organ.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

In some embodiments, the present invention provides a method further including sensing one or more conditions that affect balance, and wherein the selectively controlling the plurality of light signals includes controlling the light signals, at least partly based on the sensed one or more conditions that affect balance, to provide a sense-of-balance nerve stimulation.

In some embodiments, the sensing of the one or more conditions that affect balance includes sensing motion and orientation.

In some embodiments, the sensing the one or more conditions that affect balance includes monitoring muscular stimulation.

In some embodiments, electrical stimulation delivered via nerves connected to muscles is sensed. In some embodiments, the result of the muscular movement is sensed.

In some embodiments of the invention, monitoring muscular stimulation includes monitoring eye movements.

In some embodiments, electrical stimulation delivered via nerves connected to eye muscles is sensed. In some embodiments, the eye movement is sensed to indirectly sense eye muscle stimulation.

In some embodiments, the present invention provides an apparatus that includes one or more laser light sources configured to generate a plurality of light signals; and a transmission medium configured to transmit the plurality of light signals from the one or more laser light sources to one or more nerves of each of one or more inner-ear vestibular organs of a living animal; a controller to selectively control the plurality of light signals from each of the one or more infrared-laser light sources such that the light signals provide controlled optical stimulation to the one or more nerves in order to control nerve action potentials (NAPS) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the control of the light signals provided by the controller includes selective control of a pulse width of the plurality of light signals.

In some embodiments, the control of the light signals provided by the controller includes selective control of a duty cycle of the plurality of light signals.

In some embodiments, the control of the light signals provided by the controller includes selective control of an on-time and an off-time of the plurality of light signals.

In some embodiments, the control of the light signals provided by the controller includes selective control of a wavelength of the plurality of light signals.

In some embodiments, the control of the light signals provided by the controller includes selective control of a pulse repetition rate of the plurality of light signals.

In some embodiments, the control of the light signals provided by the controller includes selective control of a pulse shape of the plurality of light signals.

In some embodiments, the control of the light signals provided by the controller includes selective control of a minimum light intensity and a maximum light intensity of the plurality of light signals.

In some embodiments, the control of the light signals provided by the controller includes selective control of a DC background amount of light intensity of the plurality of light signals.

In some embodiments, the control of the light signals provided by the controller includes selective control of a precharge amount of light intensity followed by a trigger amount of light intensity amount of light intensity of the plurality of light signals.

In some embodiments, the control of the light signals provided by the controller includes selective control of the plurality of light signals to delay at least some of the NAPs produced by the one or more nerves that would otherwise occur.

In some embodiments, the control of the light signals provided by the controller includes selective control of the plurality of light signals to increase a frequency of the NAPs produced by the one or more nerves that would otherwise occur.

In some embodiments, the control of the light signals provided by the controller includes selective control of the plurality of light signals to decrease a frequency of the NAPs produced by the one or more nerves that would otherwise occur.

In some embodiments, the apparatus includes an implanted a self-contained battery-powered laser light-generation device.

In some embodiments, the obtaining the plurality of light signals includes implanting self-contained infrared (IR) laser device.

In some embodiments, the a transmission medium configured to transmit light signals from the one or more laser light sources to one or more nerves of each of one or more inner-ear vestibular organs of a living animal includes one or more optical fibers configured to guide the light signals.

In some embodiments, the one or more laser light sources include a first light source and a second light source, wherein the control of the light signals provided by the controller includes selective control of the first light source to send a first series of pulses during a first period of time and selective control of the second light source to send a second series of pulses during the first period of time, and wherein the first series of pulses differs from the second series of pulses in repetition rate.

In some embodiments, the present invention provides an apparatus further including at least one sensor configured to sense one or more conditions that affect balance, and wherein the control of the light signals provided by the controller includes selective control of the light signals to provide a sense-of-balance nerve stimulation at least partly based on a signal from the at least one sensor.

In some embodiments, the at least one sensor includes a motion sensor.

In some embodiments, the at least one sensor includes an orientation sensor.

In some embodiments, the at least one sensor includes a muscular stimulation monitor.

In some embodiments, electrical stimulation carried via efferent nerves to muscles is sensed. In some embodiments, the result of the muscular movement is sensed.

In some embodiments, the muscular stimulation monitor includes a sensor that monitors eye movements.

In some embodiments, the present invention provides an apparatus that includes means for obtaining a plurality of light signals from one or more laser light sources; and means for delivering the plurality of light signals to one or more nerves of each of one or more inner-ear vestibular organs of a living animal; means for selectively controlling the plurality of light signals to optically stimulate the one or more nerves in order to control nerve action potentials (NAPS) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the means for selectively controlling the light signals includes means for controlling a pulse width of the plurality of light signals.

In some embodiments, the means for selectively controlling the light signals includes means for controlling a duty cycle of the plurality of light signals.

In some embodiments, the means for selectively controlling the light signals includes means for controlling an on-time and an off-time of the plurality of light signals.

In some embodiments, the means for selectively controlling the light signals includes means for controlling a wavelength of the plurality of light signals.

In some embodiments, the means for selectively controlling the light signals includes means for controlling a pulse repetition rate of the plurality of light signals.

In some embodiments, the means for selectively controlling the light signals includes means for controlling a pulse shape of the plurality of light signals.

In some embodiments, the means for selectively controlling the light signals includes means for controlling a minimum light intensity and a maximum light intensity of the plurality of light signals.

In some embodiments, the means for selectively controlling the light signals includes means for controlling a DC background amount of light intensity of the plurality of light signals.

In some embodiments, the means for selectively controlling the light signals includes means for controlling a pre-charge amount of light intensity followed by a trigger amount of light intensity of the plurality of light signals.

In some embodiments, the means for selectively controlling the light signals includes means for controlling the light signals to delay at least some of the NAPs produced by the one or more nerves that would otherwise occur without the plurality of light signals.

In some embodiments, the means for selectively controlling the light signals includes means for controlling the light signals to increase a frequency of the NAPs produced by the one or more nerves that would otherwise occur without the plurality of light signals.

In some embodiments, the means for selectively controlling the light signals includes means for controlling the light signals to decrease a frequency of the NAPs produced by the one or more nerves that would otherwise occur without the plurality of light signals.

In some embodiments, the means for obtaining the plurality of light signals includes implanting a self-contained battery-powered laser-light-generation device.

In some embodiments, the obtaining the plurality of light signals includes implanting self-contained infrared (IR) laser device.

In some embodiments, the means for delivering the plurality of light signals to one or more nerves of each of one or more inner-ear vestibular organs includes using one or more optical fibers to guide the light signals.

In some embodiments, the one or more laser light sources include a first light source and a second light source, wherein the means for selectively controlling the plurality of light signals includes means for controlling the first light source to send a first series of pulses during a first period of time and means for controlling the second light source to send a second series of pulses during the first period of time, and wherein the first series of pulses differs from the second series of pulses in repetition rate.

In some embodiments, the present invention provides an apparatus further including means for sensing one or more conditions that affect balance, and wherein the means for selectively controlling the plurality of light signals includes means for controlling the light signals, at least partly based on the sensed one or more conditions that affect balance, to provide a sense-of-balance nerve stimulation.

In some embodiments, the means for sensing of the one or more conditions that affect balance includes means for sensing motion and orientation.

In some embodiments, the means for sensing the one or more conditions that affect balance includes means for monitoring muscular stimulation.

In some embodiments, electrical stimulation delivered via nerves connected to muscles is sensed. In some embodiments, the result of the muscular movement is sensed.

In some embodiments, the means for monitoring muscular stimulation includes means for monitoring eye movements.

In some embodiments, electrical stimulation delivered via nerves connected to eye muscles is sensed. In some embodiments, the eye movement is sensed to indirectly sense eye muscle stimulation.

In some embodiments, electrical stimulation to eye muscles is sensed. In some embodiments, the eye movement is sensed to indirectly sense eye muscle stimulation.

In some embodiments, the present invention provides a method that includes obtaining light from an optical source; and transmitting the light to respective nerves of each of a plurality of inner-ear balance organs of an animal. The animal can either be a human or be some other animal.

In some embodiments, the transmitting includes transmitting different amounts of the light through optical fibers to stimulate respective nerves of each of the plurality of inner-ear balance organs.

In some embodiments, the transmitting includes transmitting different wavelengths of the light to stimulate respective nerves of each of the plurality of inner-ear balance organs.

In some embodiments, various parameters are adjusted and/or controlled, such as the pulse repetition rate or pattern, the pulse width, the pulse intensity, the wavelength(s), the amount of background constant (DC) optical level, and/or selected multiple simultaneous wavelengths. Multiple wavelengths are provided, in some embodiments, by using a plurality of lasers having different wavelengths. In some embodiments, a plurality of fibers is used to deliver the stimulation light to a plurality of stimulation sites.

In some embodiments, the present invention includes triggers and sensors that generate signals that are input to software of the present invention, wherein the software analyzes the signals and based on the analysis, generates control signals that control the parameters, such as frequency and intensity of light output (e.g., laser pulses) for each of one or more channels that communicate with the vestibular nucleus. For example, some embodiments use sensors such as described in U.S. Pat. No. 6,546,291 issued to Merfeld et al. on Apr. 8, 2003, which was described above and which is incorporated herein by reference. For example, some embodiments include sensors for detecting characteristics of the patient's head, eyes, posture and the like.

Some embodiments use one or more implanted VCSEL arrays to directly stimulate the desired nerves, while in other embodiments, one or more implanted VCSELs are optically coupled using one or more optical fibers leading to the stimulation sites.

In other embodiments, one or more VCSEL arrays are located external to the patient's body, and use transcutaneous coupling to one or more implanted fiber arrays. In some embodiments, the implanted fiber arrays provide one or more feedback loops (e.g., a fiber having both of its ends facing outwards from the body) in order to assist coupling alignment. In some embodiments, permanent magnets are used on the implanted fiber arrays and external VCSEL stimulator to maintain coupling and assist in coupling alignment. In some embodiments, the implanted fiber arrays have a bulbous head on each fiber to collect and direct laser light into the fiber core.

Some embodiments provide programmable and/or reprogrammable control. In some embodiments, the controller is implanted in the body, and in some other embodiments, the controller is located external to the body and coupled to an implanted fiber array using transcutaneous coupling (e.g., some embodiments use a VCSEL array to provide light from the stimulator_.

In some embodiments, electrical signals of the nerves are sensed and used to provide feedback to the controller, in order to better control the laser stimulation signal.

In some embodiments, the optical nerve stimulation is used to supplement or override the nerve responses generated by the inner ear organs. Some conditions, e.g., Benign Paroxysmal Positional Vertigo (BPPV), result from over stimulation of nerves in a normally resting position. Through additional optical nerve stimulation, the natural nerve responses can be supplemented or overridden. In some embodiments, wider pulse width optical nerve stimulations are used to override or reduce the frequency of natural nerve responses to treat some inner ear conditions.

In some embodiments, the obtaining light includes implanting a self-contained infrared laser device.

In some embodiments, the obtaining light includes implanting a self-contained battery-powered device.

In some embodiments, the animal is a human person. In some embodiments, the animal is not human. Some embodiments further include sensing a condition that affects balance, and wherein the transmitting includes transmitting different light signals to each of a plurality of different balance-sense organs to provide the person sense-of-balance nerve stimulation.

In other embodiments, the present invention provides an apparatus that includes an optical source; and a transmission medium configured to transmit light from the optical source to respective nerves of each of a plurality of inner-ear balance organs of an animal.

In some embodiments, the transmission medium includes a plurality of optical fibers, and the optical source couples different amounts of the light through the plurality of optical fibers to stimulate different respective nerves of each of the plurality of inner-ear balance organs.

In some embodiments, the optical source couples different wavelengths of the light to stimulate different respective nerves of each of the plurality of inner-ear balance organs.

In some embodiments, the optical source includes a self-contained implantable infrared laser device.

In some embodiments, the optical source includes a self-contained battery-powered device.

In some embodiments, the animal is a human person. Some embodiments further include at least one sensor configured to sense a condition that affects balance, and wherein the transmission medium transmits different light signals, based on the sensed condition, to each of a plurality of different balance-sense organs to provide the person sense-of-balance nerve stimulation.

In other embodiments, the present invention provides an apparatus that includes means for obtaining light from an optical source; and means for transmitting the light to respective nerves of each of a plurality of inner-ear balance organs of an animal.

In some embodiments of the apparatus, the means for transmitting includes means for transmitting different amounts of the light through optical fibers to stimulate respective nerves of each of the plurality of inner-ear balance organs. In some embodiments, the means for transmitting includes means for transmitting different wavelengths of the light to stimulate respective nerves of each of the plurality of inner-ear balance organs. In some embodiments, the means for obtaining light includes a self-contained infrared laser implantable device. In some embodiments, the means for obtaining light includes a self-contained battery-powered implantable device.

In some embodiments, the animal is a human person, and the apparatus further includes means for sensing a condition that affects balance, and wherein the means for transmitting includes means for transmitting different light signals, based on the sensed condition, to each of a plurality of different balance-sense organs to provide the person sense-of-balance nerve stimulation.

For each of the above embodiments that describe a stimulation of a vestibular organ, there are other embodiments of the present invention that stimulate any and/or all elements of the vestibular system: inner-ear vestibular organs, CN VIII, vestibular nucleus, or any other central process of animal's system.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method comprising:
   obtaining a plurality of laser-light sources configured to generate a plurality of laser-light signals including a first laser-light signal, a second laser-light signal, and a third laser-light signal;
   providing an implantable optical-emission head configured to direct the plurality of laser-light signals toward nerves of an animal, wherein the providing of the optical-emission head includes providing a plurality of optical-output ports that emit light from a first emitting surface of the optical-emission head, wherein the plurality of optical-output ports includes a first optical-output port, a second optical-output port, and a third optical-output port;
   coupling the plurality of laser-light sources to the optical-emission head using a plurality of optical waveguides including a first optical waveguide carrying the first laser-light signal to the first optical-output port, a second optical waveguide carrying the second laser-light signal to the second optical-output port, and a third optical waveguide carrying the third laser-light signal to the third optical-output port;
   implanting the optical-emission head in the animal such that the plurality of optical-output ports of the optical-emission head directs the plurality of laser-light signals toward the nerves of the animal;
   outputting the plurality of laser-light signals from the plurality of optical-output ports to the nerves of the animal;
   testing the implanted optical-emission head to determine which selected subset of the plurality of optical-output ports is most effective for optical stimulation of desired nerves of the nerves, wherein the testing causes selected subsets of laser-light sources of the plurality of laser-light sources to emit laser-light signals from the plurality of optical-output ports toward the nerves, wherein the testing includes sensing conditions that affect balance of the animal during the testing, wherein the conditions are related to nerve action potentials (NAPs) triggered in the nerves by the laser-light signals emitted during the testing, wherein the most-effective selected subset of the plurality of optical-output ports is determined at least partly based on the sensing of the conditions; and
   selectively controlling the plurality of laser-light signals from each of the plurality of laser-light sources such that the plurality of laser-light signals provide controlled optical stimulation to the desired nerves in order to trigger nerve-action potentials (NAPS) in the desired nerves, wherein the selectively controlling includes using results of the testing of the implanted optical-emission head such that the selectively controlling of the plurality of laser-light signals results in the optical-emission head emitting laser-light signals from the selected subset of the plurality of optical-output ports that was determined to be most effective for optical stimulation of the desired nerves.

2. The method of claim 1, wherein the plurality of optical waveguides includes a plurality of optical fibers, the method further comprising assembling the plurality of optical fibers in an optical-fiber bundle.

3. The method of claim 1, wherein the selectively controlling of the plurality of laser-light signals includes controlling a pulse width of the plurality of laser-light signals.

4. The method of claim 1, wherein the selectively controlling of the plurality of laser-light signals includes controlling a pulse-repetition rate of the plurality of laser-light signals.

5. The method of claim 1, wherein the selectively controlling of the plurality of laser-light signals includes controlling a pulse shape of the plurality of laser-light signals.

6. The method of claim 1, wherein the selectively controlling of the plurality of laser-light signals includes controlling a DC background amount of light intensity and a maximum intensity of the plurality of laser-light signals.

7. The method of claim 1, wherein the selectively controlling of the plurality of laser-light signals includes controlling a precharge amount of light intensity followed by a trigger amount of light intensity of the plurality of laser-light signals.

8. The method of claim 1, wherein the selectively controlling of the plurality of laser-light signals includes controlling the plurality of laser-light signals to decrease a frequency of the NAPs produced by the nerves that would otherwise occur without the plurality of laser-light signals.

9. The method of claim 1, wherein the obtaining of the plurality of laser-light signals includes implanting a self-contained battery-powered laser-light-generation device in the animal.

10. The method of claim 1, further comprising delivering electrical stimulation to an inner-ear organ of the animal.

11. The method of claim 1, wherein the nerves of the animal are nerves of an inner-ear vestibular organ of the animal.

12. A method for optical stimulation of a plurality of nerves of a human person, the method comprising:
providing an optical-emission head having a plurality of vertical-cavity surface-emitting lasers (VCSELs) located on a first emitting face of the optical-emission head and configured to emit a plurality of laser-light signals from the first emitting face toward the plurality of nerves of the person, wherein the plurality of laser-light signals are configured to optically stimulate responses in the plurality of nerves;
implanting the optical-emission head in the person;
outputting the plurality of laser-light signals from the optical-emission head to the plurality of nerves of the person;
testing the implanted optical-emission head to determine which selected subset of the plurality of VCSELs is most effective for optical stimulation of desired nerves of the plurality of nerves, wherein the testing causes selected subsets of the plurality of VCSELs to emit laser-light signals toward the plurality of nerves, wherein the testing includes sensing conditions that affect balance of the person during the testing, wherein the conditions are related to nerve action potentials (NAPs) triggered in the plurality of nerves by the laser-light signals emitted during the testing, and wherein the most effective selected subset of the plurality of VCSELs is determined at least partly based on the sensing of the conditions; and
selectively controlling the plurality of laser-light signals emitted from each of the plurality of VCSELs such that the plurality of laser-light signals provide controlled optical stimulation to the desired nerves in order to trigger nerve action potentials (NAPs) in the desired nerves, wherein the selectively controlling includes using results of the testing of the implanted optical-emission head such that the selectively controlling of the plurality of laser-light signals results in the optical-emission head emitting laser-light signals from the selected subset of the plurality of VCSELs that was determined to be most effective for optical stimulation of the desired nerves.

13. The method of claim 12, wherein the selectively controlling of the plurality of laser-light signals includes controlling a pulse width of the plurality of laser-light signals.

14. The method of claim 12, wherein the selectively controlling of the plurality of laser-light signals includes controlling a pulse repetition rate of the plurality of laser-light signals.

15. The method of claim 12, wherein the selectively controlling of the plurality of laser-light signals includes controlling a pulse shape of the plurality of laser-light signals.

16. The method of claim 12, further comprising delivering electrical stimulation to an inner-ear organ of the animal.

17. The method of claim 12, wherein the plurality of nerves of the human person include a plurality of vestibular nerves of the human person.

18. An apparatus comprising
a plurality of laser-light sources configured to generate a plurality of laser-light signals including a first laser-light signal, a second laser-light signal, and a third laser-light signal;
an optical-emission head configured to be implanted in an animal and to direct the plurality of laser-light signals toward nerves of the animal, wherein the optical-emission head includes a plurality of optical-output ports on a first emitting surface of the optical-emission head such that the plurality of optical-output ports direct the plurality of laser-light signals from the first emitting surface, wherein the plurality of optical-output ports includes a first optical-output port, a second optical-output port, and a third optical-output port;
means for outputting the plurality of laser-light signals from the plurality of optical-output ports to the nerves of the animal, wherein the means for outputting includes a first means for carrying the first laser-light signal to the first optical-output port, a second means for carrying the second laser-light signal to the second optical-output port, and a third means for carrying the third laser-light signal to the third optical-output port;
means for testing the optical-emission head, when implanted, to determine which selected subset of the plurality of optical-output ports is most effective for optical stimulation of desired nerves of the nerves, wherein the means for testing causes selected subsets of laser-light sources of the plurality of laser-light sources to emit laser-light signals from the plurality of optical-output ports toward the nerves, wherein the means for testing includes means for sensing conditions that affect balance of the animal during testing, wherein the conditions are related to nerve-action potentials (NAPs) triggered in the nerves by the laser-light signals emitted during the testing, wherein the most effective selected subset of the plurality of optical-output ports is determined at least partly based on sense data generated from the means for sensing; and
means for selectively controlling the plurality of laser-light signals from each of the plurality of laser-light sources such that the plurality of laser-light signals provide controlled optical stimulation to the desired nerves in order to trigger nerve-action potentials (NAPs) in the desired nerves, wherein the means for selectively controlling includes means for using results of the testing of the implanted optical-emission head such that the means for selectively controlling of the plurality of laser-light signals emits laser-light signals from the selected subset of the plurality of optical-output ports that was determined to be most effective for optical stimulation of the desired nerves.

19. The apparatus of claim 18, wherein the means for selectively controlling the plurality of laser-light signals includes means for controlling a pulse width of the plurality of laser-light signals.

20. The apparatus of claim 18, wherein the means for selectively controlling the plurality of laser-light signals includes means for controlling a pulse repetition rate of the plurality of laser-light signals.

21. The apparatus of claim 18, wherein the means for selectively controlling the plurality of laser-light signals includes means for controlling a pulse shape of the plurality of laser-light signals.

22. The apparatus of claim 18, wherein the means for selectively controlling the plurality of laser-light signals includes means for controlling a DC background amount of light intensity and a maximum light intensity of the plurality of laser-light signals.

23. The apparatus of claim 18, wherein the optical-emission head is configured to direct the plurality of laser-light signals toward nerves of an inner-ear vestibular organ of the animal.

* * * * *